(12) United States Patent
Piestun et al.

(10) Patent No.: US 10,036,735 B2
(45) Date of Patent: Jul. 31, 2018

(54) IMAGING THROUGH SCATTERING MEDIA WITH HIGH SIGNAL TO NOISE RATIO AND RESOLUTION

(71) Applicant: The Regents of The University of Colorado, A Body Corporate, Denver, CO (US)

(72) Inventors: Rafael Piestun, Boulder, CO (US); Hengyi Ju, Boulder, CO (US); Jacob Dove, Boulder, CO (US); Antonio Miguel Caravaca-Aguirre, Boulder, CO (US); Todd Murray, Golden, CO (US); Donald Conkey, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 163 days.

(21) Appl. No.: 14/913,958

(22) PCT Filed: Aug. 26, 2014

(86) PCT No.: PCT/US2014/052756
§ 371 (c)(1),
(2) Date: Feb. 23, 2016

(87) PCT Pub. No.: WO2015/031395
PCT Pub. Date: Mar. 5, 2015

(65) Prior Publication Data
US 2016/0356746 A1 Dec. 8, 2016

Related U.S. Application Data

(60) Provisional application No. 61/870,078, filed on Aug. 26, 2013.

(51) Int. Cl.
*G01N 29/44* (2006.01)
*G01N 21/00* (2006.01)
(Continued)

(52) U.S. Cl.
CPC ....... *G01N 29/2418* (2013.01); *A61B 5/0095* (2013.01); *G01N 21/1702* (2013.01);
(Continued)

(58) Field of Classification Search
CPC ........... G01N 29/2418; G01N 29/0654; G01N 29/4795; G01N 29/0672; G01N 21/1702;
(Continued)

(56) References Cited

U.S. PATENT DOCUMENTS 3,054,898 A 9/1962 Westover et al.
3,597,083 A 8/1971 Fraser
(Continued)

FOREIGN PATENT DOCUMENTS

WO 2007116365 A2 10/2007

OTHER PUBLICATIONS

Vellekoop I.M., "Focusing coherent light through opaque strongly scattering media", Optics Letters, Aug. 15, 2007, vol. 32, No. 16.
(Continued)

*Primary Examiner* — Helen Kwok
(74) *Attorney, Agent, or Firm* — Maschoff Brennan; Paul G. Johnson

(57) ABSTRACT

Systems and methods are disclosed to enhance three-dimensional photoacoustic imaging behind, through, or inside a scattering material. Some embodiments can increase the optical fluence in an ultrasound transducer focus and/or enhance the optical intensity using wavefront shaping before the scatterer. The photoacoustic signal induced by an object placed behind the scattering medium can serve as feedback to optimize the wavefront, enabling one order of magnitude
(Continued)

enhancement of the photoacoustic amplitude. Using the enhanced optical intensity, the object can be scanned in two dimensions and/or a spot can be scanned by re-optimizing the wavefront before post-processing of the data to reconstruct the image. The temporal photoacoustic signal provides information to reconstruct the third-dimensional information.

20 Claims, 19 Drawing Sheets

(51) Int. Cl.
G01N 29/24 (2006.01)
A61B 5/00 (2006.01)
G01N 21/17 (2006.01)
G01N 29/06 (2006.01)

(52) U.S. Cl.
CPC . *G01N 29/0654* (2013.01); *G01N 2021/1706* (2013.01); *G01N 2201/0675* (2013.01)

(58) Field of Classification Search
CPC ............... G01N 21/49; G01N 21/1717; G01N 21/4795; G01N 21/45; G01N 21/39; A61B 5/0095; A61B 5/0059
See application file for complete search history.

(56) References Cited

U.S. PATENT DOCUMENTS

| | | | |
|---|---|---|---|
| 3,901,595 A | 8/1975 | Helava et al. | |
| 3,961,851 A | 6/1976 | Gerharz | |
| 4,178,090 A | 12/1979 | Marks et al. | |
| 4,471,785 A | 9/1984 | Wilson et al. | |
| 4,573,191 A | 2/1986 | Kidode et al. | |
| 4,794,550 A | 12/1988 | Greivenkamp, Jr. | |
| 4,825,263 A | 4/1989 | Desjardins et al. | |
| 4,843,631 A | 6/1989 | Steinpichier et al. | |
| 5,076,687 A | 12/1991 | Adelson | |
| 5,102,223 A | 4/1992 | Uesugi et al. | |
| 5,193,124 A | 3/1993 | Subbarao | |
| 5,243,351 A | 9/1993 | Rafanelli et al. | |
| 5,337,181 A | 8/1994 | Kelly | |
| 5,521,695 A | 5/1996 | Cathey, Jr. et al. | |
| 5,701,185 A | 12/1997 | Reiss et al. | |
| 6,175,416 B1* | 1/2001 | Maris ................. | G01N 21/1702 356/432 |
| 6,344,893 B1 | 2/2002 | Mendlovic et al. | |
| 6,668,654 B2* | 12/2003 | Dubois .................... | G01H 3/00 356/502 |
| 6,969,003 B2 | 11/2005 | Havens et al. | |
| 7,342,717 B1 | 3/2008 | Hausmann et al. | |
| 7,604,981 B1 | 10/2009 | Harris, Jr. et al. | |
| 7,705,970 B2 | 4/2010 | Piestun et al. | |
| 7,969,576 B1* | 6/2011 | Buckley ................ | G01J 3/4338 356/437 |
| 8,620,065 B2 | 12/2013 | Piestun et al. | |
| 8,693,742 B2 | 4/2014 | Piestun et al. | |
| 2003/0035105 A1 | 2/2003 | Quist et al. | |
| 2003/0061035 A1 | 3/2003 | Kadmbe | |
| 2003/0096220 A1 | 5/2003 | Lafferty et al. | |
| 2004/0125373 A1 | 7/2004 | Oldenbourg et al. | |
| 2005/0057744 A1 | 3/2005 | Pohle et al. | |
| 2006/0126921 A1 | 6/2006 | Shorte et al. | |
| 2006/0158956 A1* | 7/2006 | Lagharn, Jr. .......... | B01F 11/02 366/127 |
| 2007/0015992 A1* | 1/2007 | Filkins ................. | A61B 5/0073 600/407 |
| 2007/0121107 A1 | 5/2007 | Tsai et al. | |
| 2007/0268366 A1 | 11/2007 | Raskar et al. | |
| 2008/0094633 A1* | 4/2008 | Dimarzio ........... | G01N 21/4795 356/450 |
| 2008/0137059 A1 | 6/2008 | Piestun et al. | |
| 2009/0206251 A1 | 8/2009 | Hess et al. | |
| 2009/0244090 A1 | 10/2009 | Zhang et al. | |
| 2010/0278400 A1 | 11/2010 | Piestun et al. | |
| 2011/0002530 A1 | 1/2011 | Zhuang et al. | |
| 2011/0216311 A1* | 9/2011 | Kachanov .......... | G01N 21/1702 356/213 |
| 2011/0249866 A1 | 10/2011 | Piestun et al. | |
| 2011/0310226 A1 | 12/2011 | McEldowney | |
| 2012/0029829 A1* | 2/2012 | Li ........................ | A61B 5/0059 702/19 |
| 2012/0062708 A1 | 3/2012 | Johnson et al. | |
| 2012/0127557 A1* | 5/2012 | Masumura ........... | A61B 5/0095 359/291 |
| 2012/0182558 A1 | 7/2012 | Masumura | |
| 2012/0273676 A1 | 11/2012 | Kuijper | |
| 2012/0300608 A1* | 11/2012 | Masumura ......... | G01N 21/4795 369/103 |
| 2013/0102865 A1* | 4/2013 | Mandelis ............. | A61B 5/0095 600/328 |
| 2013/0147925 A1 | 6/2013 | Lew et al. | |
| 2013/0280715 A1* | 10/2013 | Bornhop ................ | G01N 21/45 435/6.11 |
| 2014/0009808 A1* | 1/2014 | Wang ........................ | G02F 1/33 359/10 |
| 2014/0078566 A1 | 3/2014 | Rosen | |
| 2014/0192166 A1 | 7/2014 | Cogswell et al. | |
| 2014/0226881 A1 | 8/2014 | Piestun et al. | |
| 2015/0035946 A1 | 2/2015 | Piestun et al. | |
| 2015/0192510 A1 | 7/2015 | Piestun et al. | |
| 2015/0211983 A1* | 7/2015 | Speck ................ | G01N 21/1702 73/152.18 |
| 2016/0048963 A1 | 2/2016 | Piestun et al. | |
| 2016/0125610 A1 | 5/2016 | Piestun | |
| 2016/0231553 A1 | 8/2016 | Piestun et al. | |

OTHER PUBLICATIONS

Vellekoop I.M., "Demixing light paths inside disordered metamaterials", Optics Express, Jan. 7, 2008, vol. 16, No. 1.
X. Xu, "Time-reversed ultrasonically encoded optical focusing into scattering media", Nature Photonics 5, Jan. 16, 2011, 154-157.
K. Si., "Breaking the spatial resolution barrier via iterative sound-light interaction in deep tissue microscopy", Scientific Reports, Oct. 19, 2012.
Chaigne, T., "Controlling Light in Scattering Media Noninvasively Using the Photo-acoustic Transmission-matrix", no date.
Conkey, D.B., "Genetic algorithm optimization for focusing through turbid media in noisy environments", Optics Express, Feb. 27, 2012, vol. 20, No. 5.
Conkey, D.B., "High-speed scattering medium characterization with application to focusing light through turbid media", Optics Express, Jan. 16, 2012, vol. 20, No. 2.
Yang, Xin, "Three-dimensional scanning microscopy through thin turbid media", Optics Express, Jan. 30, 2012, vol. 20, No. 3.
Popoff, S.M., "Measuring the Transmission Matrix in Optics: An Approach to the Study and Control of Light Propagation in Disordered Media", Physical Review Letters, Mar. 12, 2010, PRL 104, 100601.
Yaqoob, Z., "Optical phase conjugation for turbidity suppression in biological samples", Nat Photonics, Jun. 1, 2009.
Si, K., "Fluorescence imaging beyond the ballistic regime by ultrasound pulse guided digital phase conjugation", Nat Photonics, Oct. 1, 2012, 657-661.
Katz, O., "Focusing and compression of ultrashort pulses through scattering media", Nature Photonics 5, May 22, 2011, 372-377.
Judkewitz, B., "Speckle-scale focusing in the diffusive regime with time reversal of variance-encoded light", Nature Photonics, Mar. 17, 2013, 300-305.
Kong, F. "Photoacoustic-guided convergence of light through optically diffusive media", Opt. Lett. 36, 2053-5 (2011).
International Search Report and Opinion, dated Dec. 12, 2014 in PCT Application No. PCT/US2014/052756.
Chasles, F. et al., "Full-Field Optical Sectioning and Three-Dimensional Localization of Fluorescent Particles Using Focal Plane Modulation," Optics Letters, vol. 31, No. 9, May 1, 2006, 3 pgs.

(56) References Cited

OTHER PUBLICATIONS

Dowski, Jr., Edward R. et al., "Single-Lens Single-Image Incoherent Passive-Ranging Systems," Applied Optics, vol. 33, No. 29, Oct. 10, 1994, 12 pgs.
Greengard, Adam et al., "Depth From Diffracted Rotation," Optics Letters, vol. 31, No. 2, Jan. 15, 2006, 3 pgs.
Greengard, Adam et al., "Depth From Rotating Point Spread Functions," Proceedings of SPIE, vol. 5557, 2004, 7 pgs.
Greengard, Adam et al., "Fisher Information of 3D Rotating Point Spread Functions," Computational Optical Sensing and Imaging Presentation, Jun. 6, 2005, 31 pages.
Johnson, Gregory E. et al., "Passive Ranging Through Wave-Front Coding: Information and Application," Applied Optics, vol. 39, No. 11, Apr. 10, 2000, 11 pgs.
Juette, "Three-dimensional sub-1 00 nm resolution fluorescence microscopy of thick samples," 2008, Nat Methods 5: 3 pgs.
Kao, H. Pin et al., "Tracking of Single Fluorescent Particles in Three Dimensions: Use of Cylindrical Optics to Encode Particle Position," Biophysical Journal, vol. 67, Sep. 1994, 10 pgs.
Pavani, et al., "Three-dimensional, single-molecule fluorescence imaging beyond the diffraction limit by using a double-helix point spread function", PNAS, Mar. 3, 2009, and online published, Feb. 11, 2009, 5 pgs.
Pavani et al., "Three dimensional tracking of fluorescent microparticles using a photon-limited double-helix response system", Optics Express, 2008, 10 pgs.
Pentland, Alex Paul, "A New Sense for Depth of Field," IEEE Transactions on Pattern Analysis and Machine Intelligence, vol. PAMI-9, No. 4, Jul. 1987, 9 pgs.
Psiestun, Rafael et al., "Wave Fields in Three Dimensions: Analysis and Synthesis," J. Opt. Soc. Am. A., vol. 13, No. 9, Sep. 1996, 12 pgs.
Sirat, Gabriel Y., "Conoscopic Holography. I. Basic Principles and Physical Basis," J. Opt. Soc. Am. A, vol. 9, No. 1, Jan. 1992, 14 pgs.
Subbarao, Murali et al., "Analysis of Defocused Image Data for 3D Shape Recovery Using a Regularization Technique," SPIE, vol. 3204, 1997, 12 pgs.
Thomann et al., "Automatic fluorescent tag detection in 30 with super-resolution: application to analysis of chromosome movement", J. of Microscopy, 2002, 16 pgs.
GB Examination Report, dated Feb. 12, 2015, as received in Application No. 1422460.4.
GB Examination Report Search Report, dated Jul. 6, 2015, as received in Application No. 1422460.4.
International Search Report and Written Opinion dated Feb. 6, 2014 in related PCT Application No. PCT/US13/47379.
International Search Report and Written Opinion dated Jul. 22, 2014 as received in Application No. PCT/US2014/029391.
International Search Report and Written Opinion dated Jan. 27, 2016 in PCT Application No. PCT/US2015/059331 (15 pages).
Aguet, Francois et al., "A Maximum-Likelihood Formalism for Sub-Resolution Axial Localization of Fluorescent Nanoparticles," Optics Express, vol. 13, No. 26, Dec. 26, 2005, 20 pgs.

\* cited by examiner

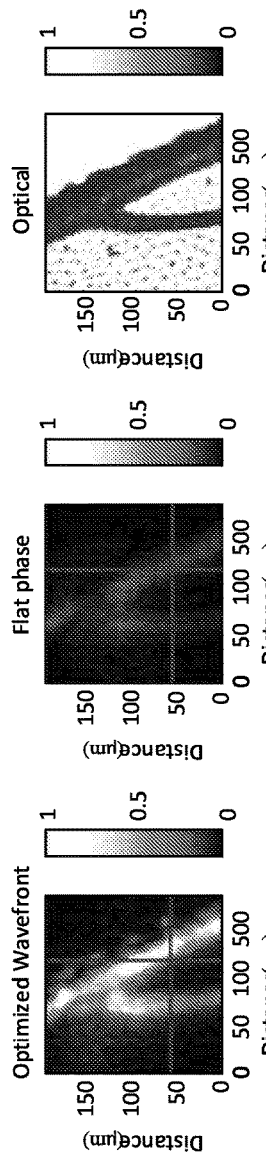
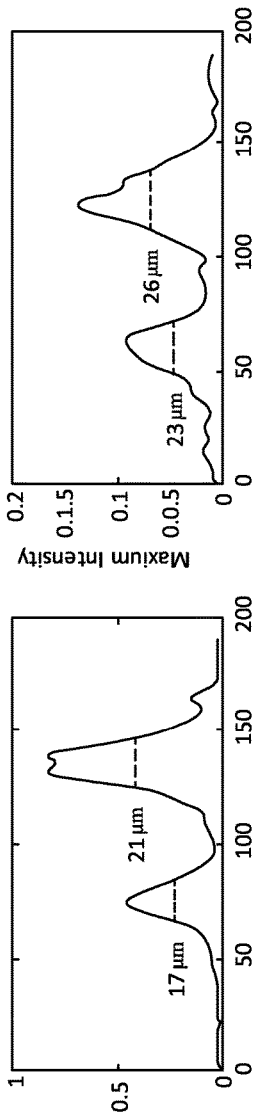
Figure 13A  Figure 13B  Figure 13C
Figure 13D  Figure 13E
Figure 13F  Figure 13G

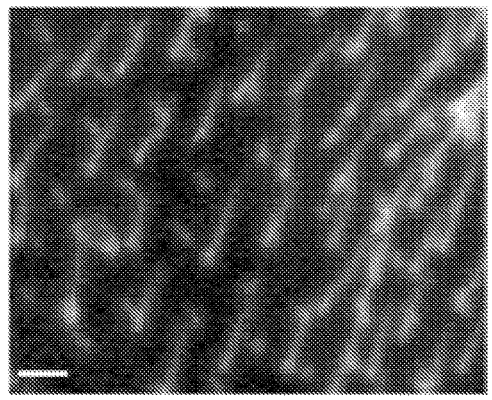
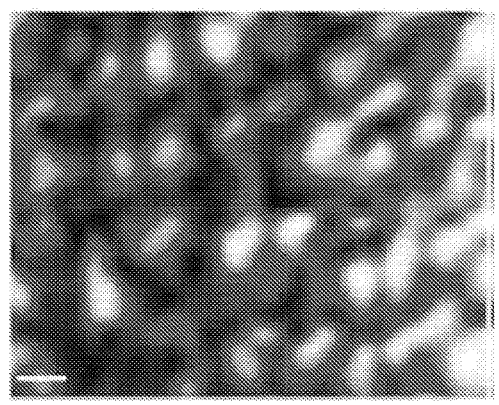
Figure 14A                Figure 14B
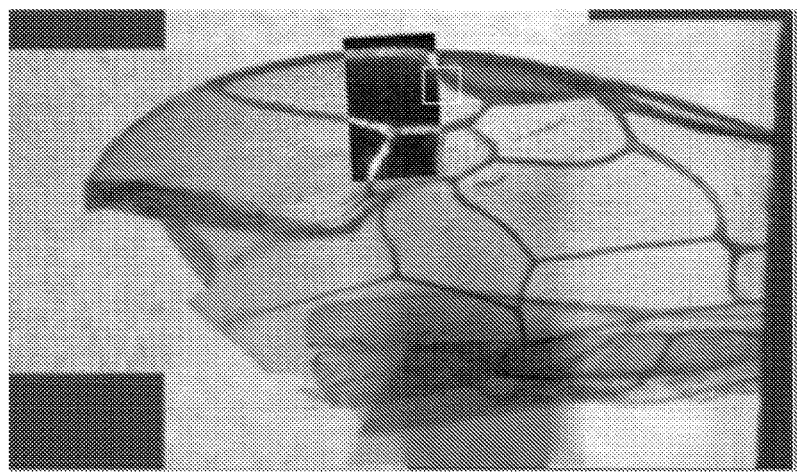
Figure 14C

IMAGING THROUGH SCATTERING MEDIA WITH HIGH SIGNAL TO NOISE RATIO AND RESOLUTION

GOVERNMENT RIGHTS

This invention was made with government support under grant number DGE0801680 awarded by the National Science Foundation. The government has certain rights in the invention.

FIELD

This disclosure relates generally to imaging through scattering media with high signal-to-noise ratio and resolution.

BACKGROUND

Scattering from turbid materials limits the depth through which images can be obtained. However, due to its deterministic nature, the scattering can be compensated with the help of a feedback mechanism using wavefront shaping. As a result, a focused spot can be created behind the scattering medium. Initial techniques have been limited by the inability to provide a feedback without access to the back side of the scatterer. Lately, new feedback mechanisms have been proposed such as iterative optimization feedback from fluorescence or digital OPC with second harmonic generation nanoparticles used as guide stars. These techniques are limited by a scarcity constraint that requires that the feedback signal only comes from a single particle to ensure single focus creation. However, this constraint can be overcome with iterative focusing methods by using a nonlinear feedback, such as two photon fluorescence, which itself is limited by optical power. Another promising method for imaging into scattering materials, especially biological tissue, uses a guide star created with an ultrasound focus. Ultrasonic waves propagate through soft tissue with three orders of magnitude less scattering than optical waves, allowing them to penetrate much deeper with minimal scattering. The ultrasound focus guide star locally modulates the frequency of light crossing it. These tagged photons are then used to record the scattered optical field, which when phase conjugated, delivers photons back to the ultrasound focus. Later, similar techniques were improved to allow for a reduction of the optical focus spot size.

A less explored feedback mechanism for focusing light through scattering materials is the photoacoustic effect. The photoacoustic effect produces acoustic waves as a medium absorbs light and undergoes thermal expansion. The photoacoustic effect is used in modern photoacoustic microscopy to image at depth in tissue. Photoacoustic microscopy differs from ultrasound imaging in that its contrast stems from optical absorption, as opposed to mechanical properties. Photoacoustics allows, for example, imaging of the vasculature by using hemoglobin in blood as the absorbing medium. Photoacoustic feedback has also been suggested for measuring the transmission matrix through a scattering material onto light-absorbing fibers. In this transmission matrix measurement the input optical modes were related to the absorbers found behind the scattering material. As a result, it was possible to localize particles along the axis of the transducer and create optical foci at the absorbers detected in the matrix. Unfortunately, none of these two early techniques has demonstrated so far imaging capability.

SUMMARY

Embodiments described herein include a method that includes illuminating a sample through a scatterer using a light source and at least one spatial light modulator; receiving a photoacoustic signal from a transducer; determining an optimized wavefront from the photoacoustic signal; modifying a configuration of the spatial light modulator based on the optimized wavefront; and illuminating the sample through the scatterer using the light source and the spatial light modulator with the modified configuration.

In some embodiments, the spatial light modulator is an optical element selected from the group consisting of one or more spatial light modulators, phase-only spatial light modulators, intensity-only spatial light modulators, prism arrays, diffractive elements, diffusers, holograms, Dammann gratings, liquid crystal spatial light modulators, phase masks, amplitude masks, acousto-optic modulator, acousto-optic deflector, and phase/amplitude masks.

In some embodiments, the modified configuration can produce an optical focus that is smaller than the acoustic focus. In some embodiments, the determining the optimized wavefront includes using an optimization algorithm to determine the optimized wavefront. In some embodiments, the method may also include scanning the sample, moving the sample with fluid, scanning a focus of the transducer, and/or scanning a focus of the light source.

An imaging system is also disclosed that includes a pulsed light source; an optical system configured to direct light from the light source toward a sample through a scatterer; one or more acoustic transducers configured to record acoustic signals from the sample; and a controller coupled with at least a portion of the optical system and the one or more acoustic transducers, wherein the controller is configured to modify the phase and/or amplitude of the light directed by the optical system through the wall using data from the one or more acoustic transducers.

In some embodiments, the one or more acoustic transducers can be disposed outside the wall such that the acoustic signals pass through the wall. In some embodiments, the optical system may include a spatial light modulator, one or more lenses and/or an objective lens.

In some embodiments, the optical system may include an optical element selected from the group consisting of one or more spatial light modulators, phase-only spatial light modulators, intensity-only spatial light modulators, prism arrays, diffractive elements, diffusers, holograms, Dammann gratings, liquid crystal spatial light modulators, phase masks, amplitude masks, acousto-optic modulator, acousto-optic deflector, and phase/amplitude masks.

In some embodiments, the controller may be configured to use a optimization algorithm based on data from the one or more acoustic transducers modify the phase and/or amplitude of the light.

In some embodiments, the controller may be configured to use spatially varying feedback to optimize an optical wavefront from the optical system such that light is enhanced and focused to a single speckle behind the wall. In some embodiments, the controller may be configured to increase the depth of optical resolution photoacoustic microscopy by providing high intensity optical focus. In some embodiments, the controller may be configured to scan the sample, scan a focus of the transducer, and/or scan a focus of the light source.

A method is also disclosed that may include illuminating a sample inside a scatterer with a plurality of optical wavefronts modulated by a spatial light modulator, each of the plurality of optical wavefronts produced modulated by the spatial light modulator using one of a plurality SLM matrices selected from a population of SLM matrices; receiving a plurality of electric signals from a transducer, wherein each of the plurality of electric signals correspond with a photoacoustic signal received at the transducer for each of the plurality of illuminations; determining an optimum SLM matrix from the population of SLM matrices based on the plurality of electric signals; and returning an image of the sample corresponding with illumination of the sample with the optimum SLM matrix.

In some embodiments, the determining an optimum SLM matrix from the population of SLM matrices comprises determining an optimum SLM matrix from the population of SLM matrices using a genetic algorithm. In some embodiments, the determining an optimum SLM matrix from the population of SLM matrices based on the plurality of electric signals comprises determining an optimum SLM matrix from the population of SLM matrices based on the peak-to-peak voltage of the plurality of electric signals. In some embodiments, the optimum SLM matrix produces an optical focus at or near the sample that is smaller than the acoustic focus.

In some embodiments, the method may include scanning the sample in the x-y plane; and repeating the method. In some embodiments, the method may include moving the focus of the transducer; and repeating the method.

In some embodiments, the image may be a three-dimensional image of the sample. In some embodiments, the plurality of electric signals may comprise a plurality of acoustic signals, wherein the acoustic signals are enhanced by nonlinear efforts in the sample.

These illustrative embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

FIGS. 13A-13G illustrate some results of an imaging example performed on a fly wing using the embodiments described herein.

FIG. 14A-C illustrate an example image of sweat bee wing hair according to some embodiments described herein.

DETAILED DESCRIPTION

Systems and methods are disclosed that use a photoacoustic feedback to optimize an optical focus for imaging a sample through a scatterer. By using photoacoustic feedback to shape the wavefront response using a spatial light modulator, in some embodiments, the focus of light through a scatterer can be optimized. This optimization can include an iterative process and/or a genetic algorithm that can improve over time based on signals representing photoacoustic measurements of the sample. The optimization may also be used for imaging various points of a target location after scanning the sample, scanning the acoustic focus location, and/or scanning the focus of light from the spatial light modulator. The optimization may result in an optical focus that is smaller than the acoustic focus of a photoacoustic transducer.

In some embodiments, non-iterative algorithms may be used. For example, the properties of a medium (or scatterer) can be measured as described above by determining an optimized SLM Matrix for each point within the sample of interest. This can be done, for example, using the so-called transmission matrix that characterizes the medium (or scatterer). With the knowledge of the transmission matrix light can be focused on arbitrary locations without using a genetic algorithm for imaging within the medium.

Moreover, by analyzing the temporal profile of a resulting photoacoustic wave, in some embodiments, a three-dimensional (3-D) image can be formed from a two-dimensional scan. Embodiments described herein may also achieve a significant improvement in signal-to-noise ratio of about one order of magnitude or more.

Furthermore, according to some embodiments described herein, high contrast photoacoustic imaging systems can combine wavefront shaping using, for example, a spatial light modulator and an ultrasound transducer. The spatial light modulator phase can encode the wavefront to maximize the intensity of light through a scatterer, while the transducer can provide feedback for an iterative optimization algorithm.

Figure 1:
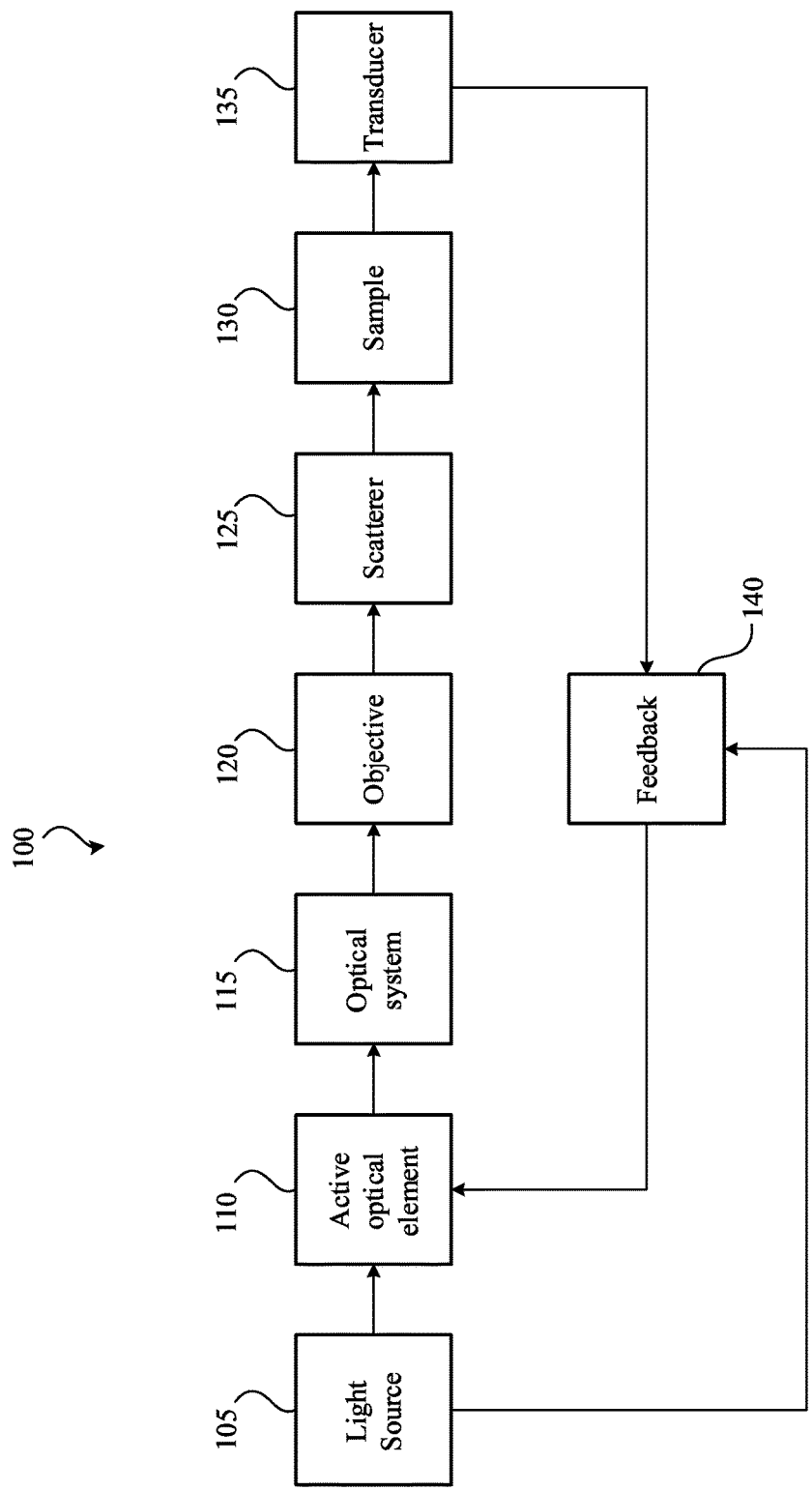
FIG. 1 illustrates a block diagram of a photoacoustic system according to some embodiments described herein.

FIG. 1 illustrates a block diagram of a photoacoustic system 100 according to some embodiments described herein. The photoacoustic system 100 includes a light source 105, a spatial light modulator 110, an optical system 115, an objective 120, a scatterer 125, a sample 130, a transducer 135, and a feedback system 140. The photoacoustic system 100 can provide a number of different imaging results. For example, the photoacoustic system 100 can provide a three-dimensional image of the sample from a two-dimensional scan. As another example, the photoacoustic system 100 can provide a high signal-to-noise image of the sample.

The light source 105 can include, for example, one or more lasers, laser diodes, collimated light sources, pulsed lasers, picosecond lasers, femtosecond lasers, etc. The light source 105 may also include a high repetition rate light source (e.g., a pulsed laser) such as, for example, a light source operating above 100 Hz. The light source may direct light onto and/or through the spatial light modulator 110.

The spatial light modulator 110 can include any optical element that can provide controllable spatially varying modulation of the light from the light source. The spatially varying modulation can include either or both phase and amplitude modulation. The spatial light modulator 110 may include, for example, acousto-optic modulator, acousto-optic deflector, electro-optic modulator, galvo-mirror, galvo-mirror array, a deformable mirror, a digital micromirror device, a liquid crystal spatial modulator, a phase-only spatial light modulator, an intensity-only spatial light modulator, etc. The spatial light modulator 110 may be a reflective spatial light modulator and/or refractive spatial light modulator. The spatial distribution of the light from the spatial light modulator 110 may be modified based on input from a controller The spatial light modulator 110 may produce a controlled response to incident light from the light source 105 based on an SLM matrix provided by the feedback system 140. Each value in a given SLM matrix can correspond with a pixel of the spatial light modulator and the value can correspond with an amplitude and/or phase of the light modulated and/or produced by the spatial light modulator. The SLM matrix may include a phase mask or wavefront.

The optical system 115 can direct light from the spatial light modulator 110 toward the objective 120. The optical system 115 can include any number and/or type of optical elements such as, for example, one or more lenses, focusing optical elements, mirrors, refractors, reflectors, filters, scatters, gratings, diffusers, prisms, prism arrays, holograms, beam splitters, polarizing devices, linear polarizers, circular polarizers, dicroic mirrors, non-linear materials, crystals, polymers, optical fibers, single mode fibers, fiber bundles, multimode fibers, etc.

The objective 120 can focus light from the optical system onto the sample through the scatterer 125. The objective can include one or more focusing optical elements such as, for example, a microscope or portions of a microscope, endoscopic objective, light delivery fiber, etc. In some embodiments, the objective 120 and the optical system 115 may be combined into a single system.

The scatterer 125 can include any type of scattering element that can produce, for example, a non-uniform optical or speckle field. The scatterer 125, for example, can include a glass diffuser, a wall, turbid media, a membrane, a skin, an opaque wall, a scattering medium, bone, a skull, tissue, a scattering wall, etc.

The sample 130 may include any sample that may be imaged by the photoacoustic system 100. The sample 130 may be disposed on the surface of or with a scanning mechanism that can move the sample 130 in the x-plane and/or the y-plane. In some embodiments, the sample 130 may also be moved using fluid such as, for example, in a microfluidic device.

The transducer 135 may include any type of acoustic transducer that converts acoustic energy waves into an electrical signal. The transducer 135 may include, for example, one or more immersion transducers, a high frequency transducer, pressure transducer, sonar transponder, ultrasonic transceiver, piezoelectric transducer, a transducers based on optical resonance shifts due to the effect of acoustic pressure, interferometer based acoustic detectors, capacitive micro-machined ultrasound transducers etc. The transducer may or may not be placed behind the scatterer 125. In some embodiments, the transducer 135 may be disposed on the same side of the scatterer 125 as the light source 105 and/or the spatial light modulator 110. In some embodiments, the sample 130 may be disposed within a medium and the transducer 135 may not be disposed with the medium.

In some embodiments, the scatterer 125, the sample 130, and/or the transducer 135 may disposed within a fluid such as, for example, alcohol, water, oil, tissue, bodily fluids, etc. In some embodiments, the scatterer 125 may include tissue or bone, and the sample 130 may be any biological sample located within or behind the tissue or bone.

In some embodiments, the transducer 135 may be located externally relative to the tissue or bone. For example, the sample 130 may be brain tissue, and the scatterer 125 may include the skull. The transducer 135 may be located outside the skull. As another example, the sample 130 may be an inner portion of the eye, and the scatterer 125 may include the outer portions of the eye such as the damaged lens by a cataract and/or the vitreous humor. The transducer 135 may be located outside the eye.

The feedback system 140 may include various electrical components that may amplify, filter, and/or measure electrical signals from the transducer 135 and/or the light source 105 and provide a feedback signal to the spatial light modulator 110 that may be used to modulate the state and/or response of the spatial light modulator 110. The feedback system 140, for example, can include one or more amplifiers, filed programmable gate arrays (FPGAs), comparators, controllers, processors, memories, user interfaces, logic, circuits, oscilloscopes, etc. The feedback system 140 may also include any or all components described in conjunction with computational system 1600. The feedback system 140 may also control the operation of the light source 105, the spatial light modulator 110, and/or the transducer as well as any other components.

The photoacoustic system 100 can maximize the photoacoustic signal produced received by the transducer 135 by modulating the wavefront produced using the spatial light modulator 110. An iterative optimization algorithm such as, for example, a process 800 shown in FIG. 8, may be used by the feedback system 140 for optimization. In some embodiments, a genetic algorithm can be used for the optimization. In the optimization algorithm, the cost function may be the peak-to-peak voltage (e.g., proportional to pressure) or the electrical current of the acoustic signal produced from the transducer in response to the acoustic wave. Using the feedback from the photoacoustic signal provided by the transducer 135, the optimization algorithm can be used to determine a state (e.g., the SLM matrix) of the spatial light modulator 110 that maximizes the cost function and/or the light intensity within the acoustic focus volume. After the optimization process the best response of the spatial light modulator 110 may be projected by the spatial light modulator 110. This optimization may occur for each position at a target near the sample 100, for different focus locations of the transducer 135, and/or for different focus positions provided by the spatial light modulator 110.

In some embodiments, the photoacoustic system 100 can image the sample 130 through the scatterer 125. Such embodiments can use wavefront optimization using photoacoustic feedback from the transducer 135 to focus the light from the light source 105 and/or the spatial light modulator 110 to image the sample 130 behind the scatterer 125 with improved signal-to-noise ratio at sub-acoustic resolution. An optical focus that is smaller than the acoustic focus can be created by taking advantage of the spatially non-uniform sensitivity of the acoustic transducer to the photoacoustic waves generated by the sub-acoustic-sized optical speckle. Using this optimized optical focus, photoacoustic images can be created with sub-acoustic resolution behind the scatterer 125 using acoustic feedback.

In some embodiments, the photoacoustic system 100 can pre-compensate for the optical wavefront resulting from the scatterer 125, and/or the light propagation can be controlled through and beyond the scatterer 125. In some embodiments, acoustic waves detected by the transducer 135 can provide a feedback mechanism for wavefront optimization that can occur at the spatial light modulator 110. The penetration of acoustic waves can be much deeper than optical waves and may not be affected by optical scattering.

In some embodiments, the scatterer can produce speckle in a target region at or surrounding the sample 130. The speckle size can be a function of the scatterer 125, the wavelength of the light, and the spatial light modulator 110. In some embodiments, the spatial light modulator can be programmed with an SLM matrix that produces a light response that results in a speckle size that is smaller than transducer focus. Since the scatterer 125 may produce a varied response to the light provided by the spatial light modulator 110, feedback from the transducer 135 can be used to optimize the spatial light modulator 110 to provide light response that may result in a speckle size that is smaller than the transducer focus.

Figure 8:
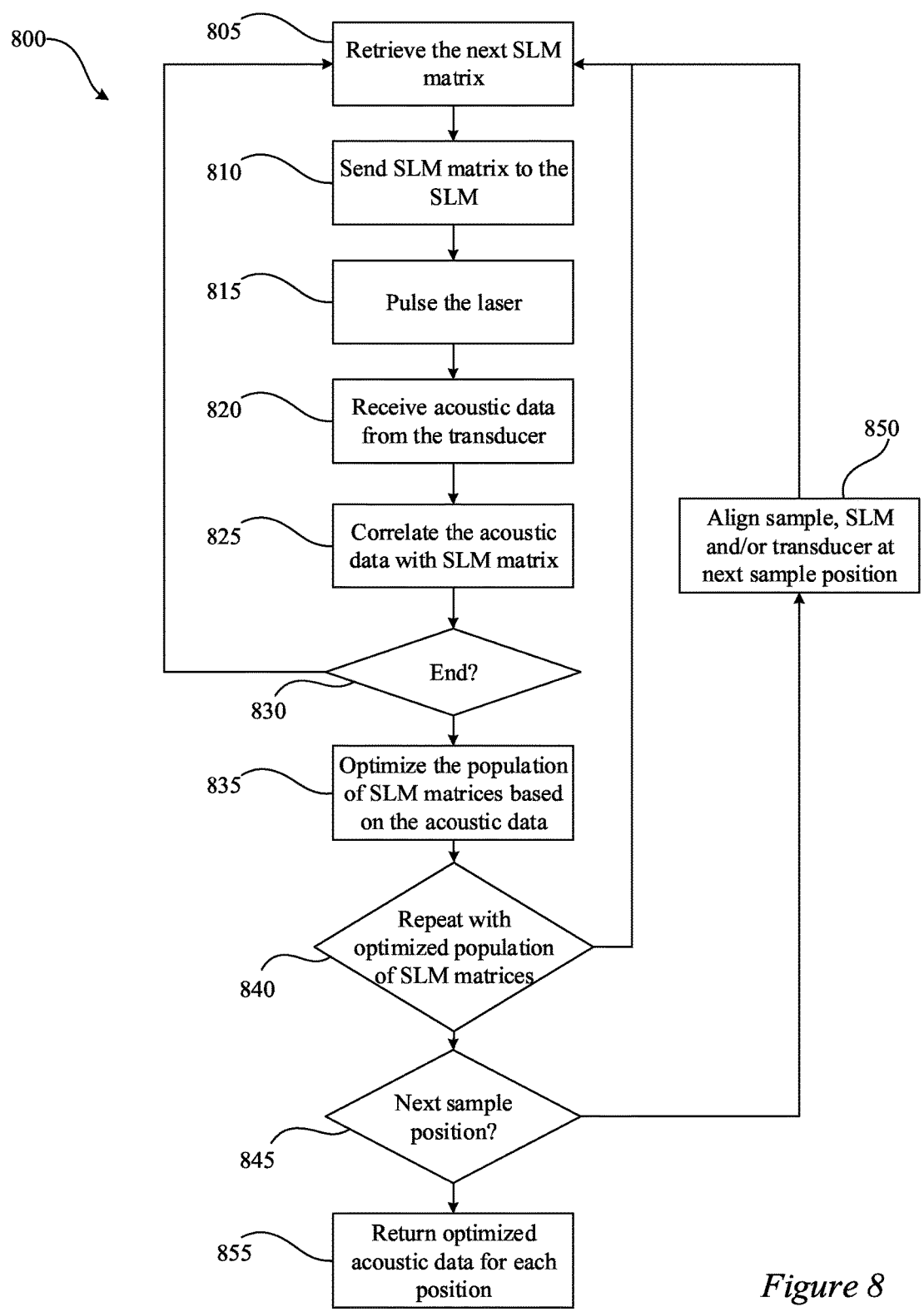
FIG. 8 is a flowchart of a process for returning an optimized image of a sample imaged through a scatterer according to some embodiments described herein.

In some embodiments, the feedback system 140 may execute a genetic algorithm to optimize the wavefront produced by the spatial light modulator 110. An example process for executing a genetic algorithm is shown in FIG. 8. The genetic algorithm may use a population of SLM matrices to optimize the wavefront produced modulated by the spatial light modulator 110. The population of SLM matrices may include a plurality (e.g., 50, 100, 150, 200, 500, 1000, etc.) of candidate SLM matrices that can be mutated and altered based on feedback from the transducer. Each value in a given SLM matrix can correspond with a pixel of the spatial light modulator and the value can correspond with an amplitude and/or phase of the light modulated and/or produced by the spatial light modulator.

The genetic algorithm can start from a population of randomly generated SLM matrices. The genetic algorithm can be an iterative process, with the population in each iteration called a generation. In each generation, the fitness of every SLM matrix in the population of SLM matrices can be evaluated in relation to the acoustic feedback. The fitness can include the intensity of the acoustic signal produced by a given SLM matrix. The more fit SLM matrices can then be selected from the current population and/or modified (re-combined and possibly randomly mutated) to form a new generation SLM matrices. The new generation of SLM matrices can then be used in the next iteration of the algorithm. Commonly, the algorithm terminates when either a maximum number of generations has been produced, or a satisfactory fitness level has been reached for the population such as, for example, a threshold value has been achieved. The process 800 in FIG. 8 includes an example genetic algorithm.

In some embodiments, the genetic algorithm may begin by creating a population of random SLM matrices (or phase masks). These SLM matrices may be ranked according to a cost function which quantifies how well each mask optimizes the photoacoustic signal. The cost function may weight, for example, the intensity of the returned acoustic signal. The genetic algorithm may continue by creating a new generation of SLM matrices by combining (e.g., mating) pairs of randomly selected SLM matrices, with a higher probability of selection given to the better performing SLM matrices. These new SLM matrices are also ranked according to the cost function. The process continues for a set number of generations to facilitate the evolution of an optimal SLM matrix.

In some embodiments, the sample can be scanned around the focus because of the speed limitations imposed by the low repetition rate of the laser. In some embodiments, with a higher repetition rate laser source and a fast spatial light modulator sub-second optimization of the input phase mask can occur. In some embodiments, the transducer 135 may be scanned rather than the sample 130. In some embodiments, one or more scanning transducer may be used for in-vivo testing of biologically relevant samples and/or increase the penetration depth of current photoacoustic microscopy techniques.

In some embodiments photoacoustic images can be created by locally enhancing fluence using photoacoustic imaging combined with wavefront shaping to locally enhance fluence and hence the image signal to noise. Furthermore, some embodiments can image in three dimensions through a highly scattering medium (without use of the no significant memory effect) and without need to access the back side of the scatterer where the object is located.

Figure 2:
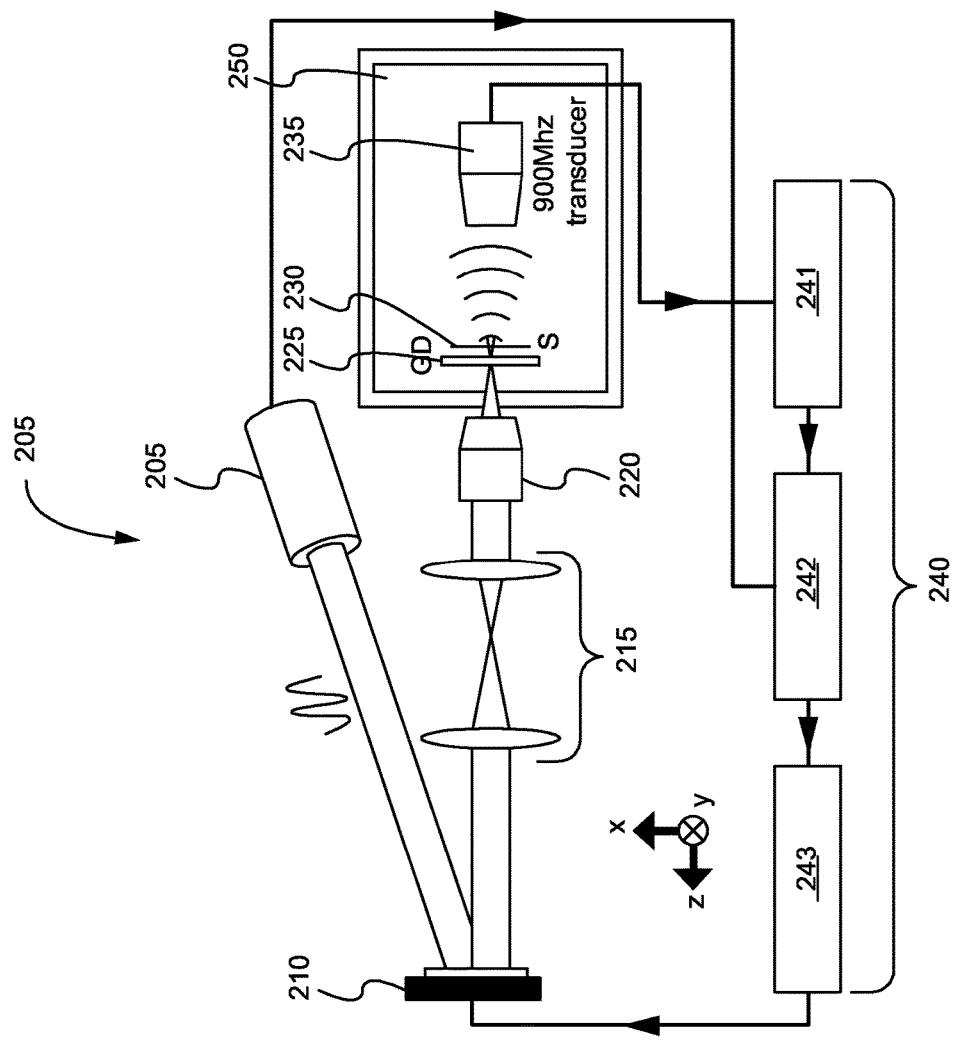
FIG. 2 illustrates a specific example of a photoacoustic system of the photoacoustic system shown in FIG. 1, according to some embodiments described herein.

FIG. 2 illustrates a photoacoustic system 200 that is a specific example of the photoacoustic system 100 shown in FIG. 1, according to some embodiments described herein. While various specific details are described in conjunction with FIG. 2, these specific details only represent one specific example of the various embodiments described herein. In the photoacoustic system 200, the light source 105 is a laser 205. The laser 205 in conjunction with the optical system 215 can produce an attenuated, expanded, and collimated 5 ns laser pulse. The laser 205, in this specific example, may include a continuum Surelight 120 laser. The laser 205 may have a 20 Hz repetition rate and/or may be an Nd:YAG frequency doubled laser that produces light at 532 nm wavelength.

The spatial light modulator 110 may include a reflective, phase-only, liquid crystal spatial light modulator 210 (e.g., Boulder Non-linear Systems, 512×512 pixels). The phase-only liquid crystal spatial light modulator 210 may be illuminated by the laser 205. Following the phase-only liquid crystal spatial light modulator 210, the energy per pulse in the beam can be about ~21 µJ. The energy per pulse can be between 1 µJ and 200 mJ. The phase-only liquid crystal spatial light modulator 210 can control the wavefront that ultimately is used to image the sample.

An optical system 215 may include a 4f optical system having two lenses (f1=150 mm, f2=250 mm). The optical system 215 may image the spatial light modulator onto the back aperture of a long working distance microscope objective 220 (Mitutoyo, 34 mm working distance, 5× magnification, 0.14 NA).

The microscope objective 220 can focus light into a water tank 250 or medium and onto the surface of scattering material 225 (e.g., glass diffuser). The scattering material 225 and/or water tank 250 can scatter the light form the illumination and optical systems. A sample 230 used for wavefront optimization and imaging can be located anywhere behind the scattering material 225 and/or mounted to a 2-D translation stage to allow for scanning in the x and y dimensions. The photoacoustic signal produced by the sample can propagate through the water and can be detected by a 90 MHz transducer 235 (e.g., Olympus, model V3512). The transducer 235 can detect the photoacoustic signal from the sample 230 that is disposed behind the scattering material 225.

Feedback system 240 may include an amplifier 241, an oscilloscope 242, and/or a computer 243. After being pre-amplified using the amplifier 241 (e.g., Femto HSA-7-2-40, low-noise 40 dB) the signal can be recorded and/or digitized and sent to the computer 243 for analysis. The signal can also be digitally high-pass filtered with any type of filter such as, for example, a 2nd order Butterworth filter with a cut-off frequency of 80 MHz to remove the low frequencies using the oscilloscope 242.

Some embodiments described herein have been used to image a polypropylene tube (90 μm inner diameter and 120 μm outer diameter) filled with India ink and placed behind a glass diffuser (scatterer 125). In one example, an optimization algorithm such as, for example, the process 800 shown in FIG. 8, runs with a population size of 20 and 804 input modes through 1200 phase mask measurements, or 60 generations, to find the optimal SLM matrix (or phase mask). The mutation rate decreased as the optimization progressed. FIG. 3A, for example, illustrates how the enhancement evolved as the optimization proceeded. The enhancement, for example, can be defined as the value of the cost function of the projected mask divided by the mean of the cost function from each member of the initial population. An amplitude enhancement of 10 of the photoacoustic signal is observed after 1200 iterations, which can be indicative of a 10-fold increase in absorbed light in the focal region.

Figure 3C:
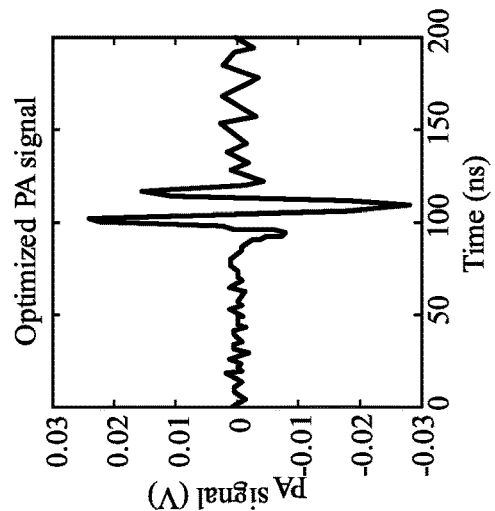
FIGS. 3B and 3C illustrate the photoacoustic response for a flat phase and the optimized phase mask are compared according to some embodiments described herein.
Figure 3B:
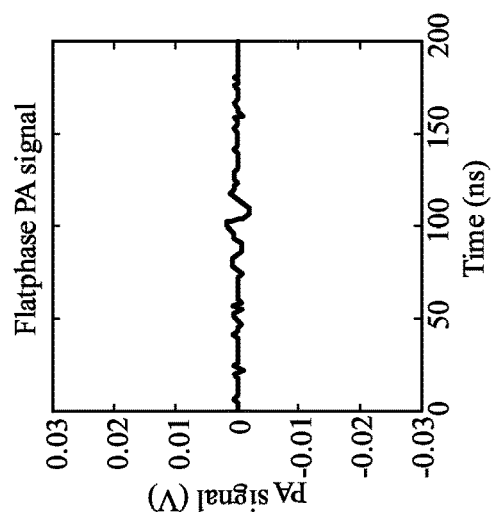
Figure 3A:
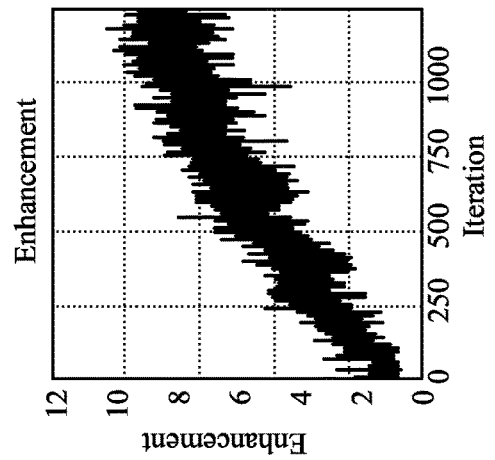
FIG. 3A illustrates how the enhancement evolved as the optimization proceeded according to some embodiments described herein.

FIGS. 3B and 3C illustrate the photoacoustic response for a flat phase and the optimized phase mask are compared. To minimize the noise of the photoacoustic signal 40 samples of the signal were averaged. As the signal strength increases the number of averaged samples decreases gradually to, for example, in order to decrease the optimization time. As a result the signals shown in FIG. 3B and FIG. 3C are taken with 40 and 5 averaged samples, respectively. In some embodiments, the optimization process may occur in real time and/or may take some processing time to complete such as, for example, about 15 minutes. In some embodiments, the time required to process the data may be limited by the repetition rate of the laser (or light source). These figures show clearly the improvement in the photoacoustic signal produced using an optimization algorithm.

Figure 4C:
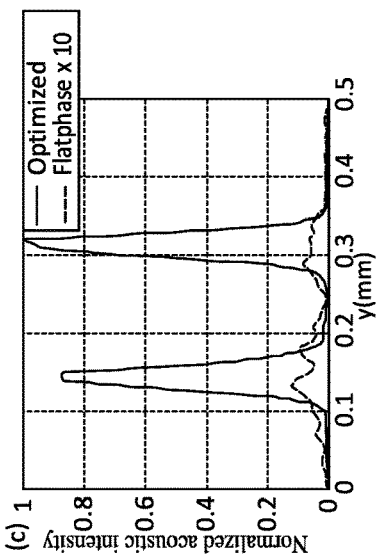
FIGS. 4A-4F illustrate some of the benefits of embodiment described herein.
Figure 4B:
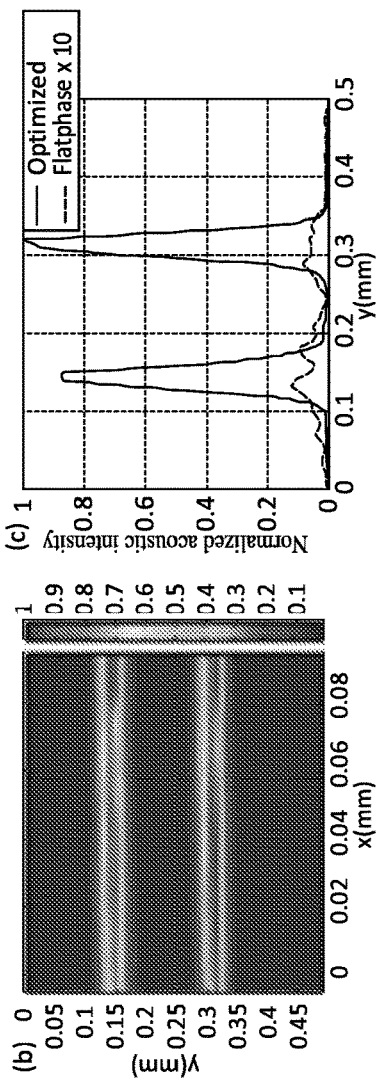
Figure 4A:
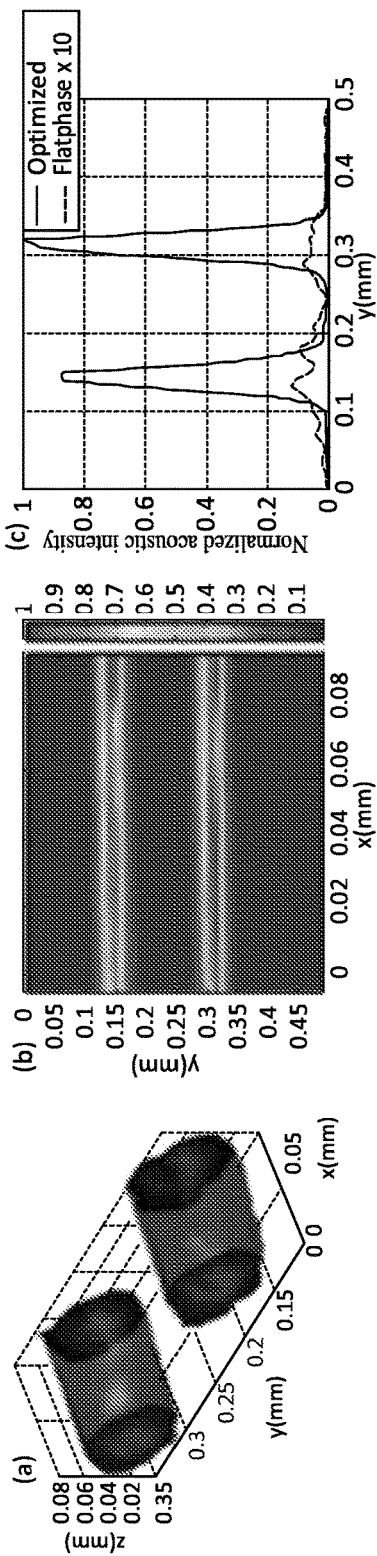

FIGS. 4A-4F illustrate some results of an imaging example performed on two polypropylene tubes using embodiments described herein. In this example, the optimization algorithm used a population size of 20 and included 804 input modes through 1200 SLM matrix measurements, or 60 generations, to find the optimal SLM matrix. After verification of photoacoustic signal enhancement, 3-D imaging can be enhanced with localized optical fluence. As a first demonstration the sample around the optimized focus with the automated translation stage can be scanned. The photoacoustic signal amplitude, recorded from each position in the x-y plane, can be processed to reconstruct the 3-D maximum intensity projection of the two tubes (FIG. 4A). The temporal profiles of the photoacoustic signal can encode the z (axial) information. By sliding a window through the signal and selecting the maximum value for each window position many z values can be fixed to each x and y position to create the third dimension. The size of the window is determined by the axial resolution, $\delta z$, of the transducer, which comes from its bandwidth, B, and the speed of sound, cs: $\delta z = c_s/B \cong 15$ μm. The transducer may also determine the transverse resolution of the acoustic beam: $BD(-6\ dB) = 1.02 \cdot Fc_s/Df \cong 36$ μm, where BD is the acoustic beam diameter at the focus plane, F is the focal distance, D is the diameter of the transducer, and f is the central frequency.

Figure 4F:
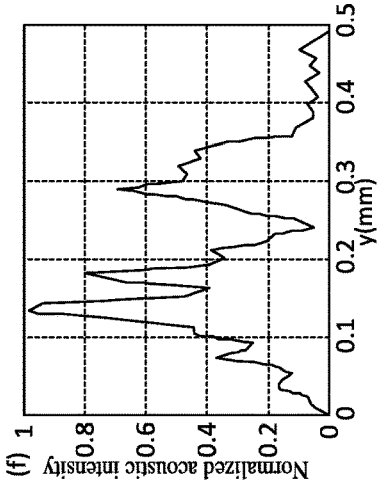
Figure 4E:
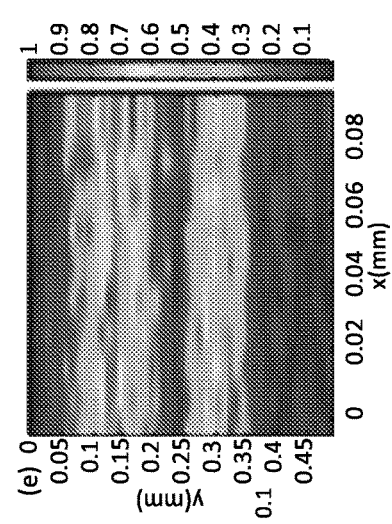
Figure 4D:
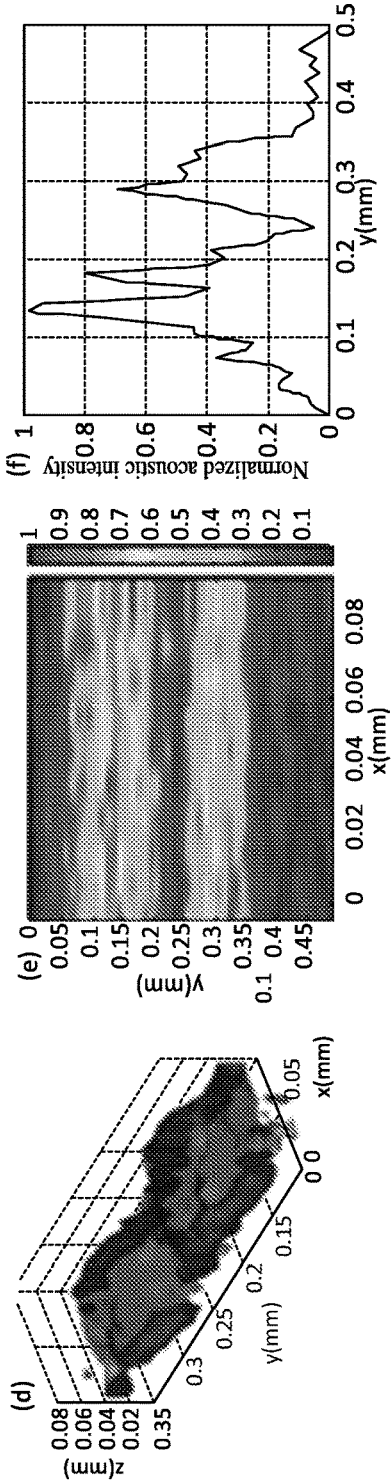

A 2-D slice can be extracted from the 3-D image to measure the distance between the two tubes. In FIG. 4B the normalized 2-D image corresponding to an intermediate plane shows the photoacoustic maximum signal from both tubes is separated by 170 μm. From the size of the outer diameter it can be inferred that the tubes are 50 μm apart. A normalized 1-D scan from the x=0.02 mm profile is shown in FIG. 4C. As the optical focus moved away from the center of the tube during the image scan procedure, the wavefront no longer matched the curvature of the tube and the focus inside the tube was destroyed, thus producing negligible signal at the tube edges. Despite this, the tubes are clearly defined with high-absorption contrast. For comparison, the 3-D, 2-D, and 1-D reconstruction with a non-optimized wavefront projected on the SLM are shown in FIGS. 4D, 4E, and 4F, respectively. In this case, the width of the two tubes and their separation remain difficult to infer. FIG. 4C also compares the photoacoustic intensities (proportional to acoustic pressure squared) of the optimized and non-optimized scans.

Some embodiments described herein can produce an order of magnitude or greater enhancement of the photoacoustic signal amplitude using an optimization algorithm (e.g., a genetic algorithm) of the phase of the input wavefront to compensate for scattering and increase the optical intensity of light in the acoustic focus. This enhancement can allow for the imaging of two 90 μm inner diameter tubes with excellent signal-to-noise ratio as compared to a flat phase wavefront. Furthermore, by using the time of arrival information from the photoacoustic signal, the depth information can be recovered and a 3-D image can be reconstructed after scanning the sample in two dimensions.

In some embodiments, with a higher repetition rate laser source and a faster wavefront modulation device sub-second optimization of the input phase mask can occur. Embodiments described herein can produce photoacoustic images created by locally enhancing optical focus using feedback from photoacoustic signals, which can enhance fluence and/or the image signal to noise. Furthermore, embodiments of the invention can image in three dimensions through a highly scattering medium (with no significant memory effect) and without need to access the back side of the scatterer where the object is located.

Figure 5A:
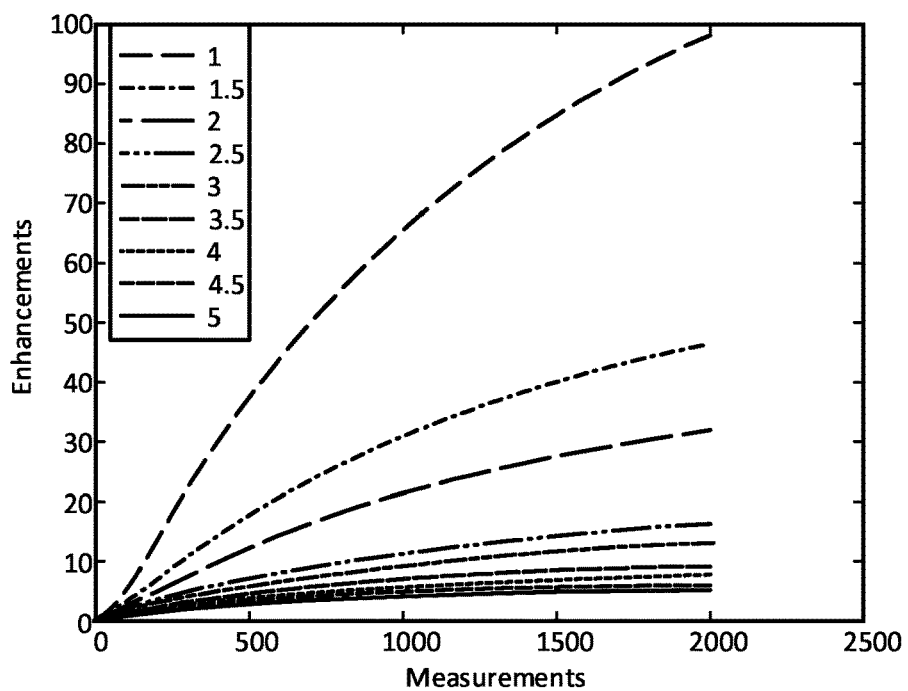
FIG. 5A shows a number of simulation results of the photoacoustic signal enhancement from an optimization algorithm according to some embodiments described herein.
Figure 5B:
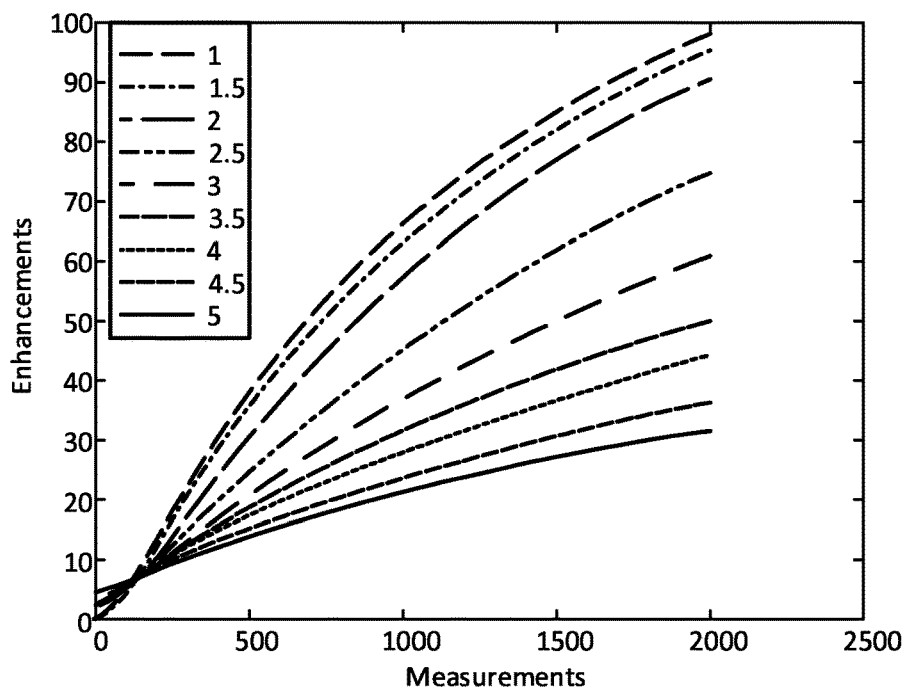
FIG. 5B shows a number of results of the optical enhancement inside the transducer focus according to some embodiments described herein.

In some embodiments, wavefront optimization using the photoacoustic feedback can enhance the photoacoustic signal by increasing the light fluence in the transducer focal region. The light distribution in the transducer focus, for example, can be determined by the optical speckle size. When the optical speckle size is smaller than the transducer focus, the optimization creates a focus whose size is smaller than the transducer focus. This can allow the system to resolve objects smaller than the acoustic resolution of the transducer using the created optical focus. FIG. 5A shows a number of simulation results of the photoacoustic signal enhancement from an optimization algorithm such as, for example, using the process 800 shown in FIG. 8. Each line represents a ratio of ultrasound transducer focus diameter to optical speckle diameter. As the ratio increases, the photoacoustic enhancement decreases. When the optical speckle is smaller than the ultrasound focus, the photoacoustic enhancement will differ from the actual optical enhancement. FIG. 5B shows a number of results of the optical enhancement inside the transducer focus. As with the PA signal, the enhancement decreases with increasing transducer focus to optical speckle size ratio. However, the decrease is not as drastic which means that an optical focus can be created with large size ratios.

Figure 6A:
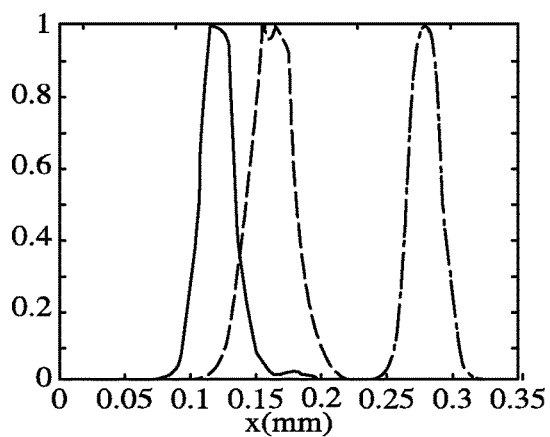
FIGS. 6A-6F illustrate some of the benefits of the embodiment described herein.
Figure 6B:
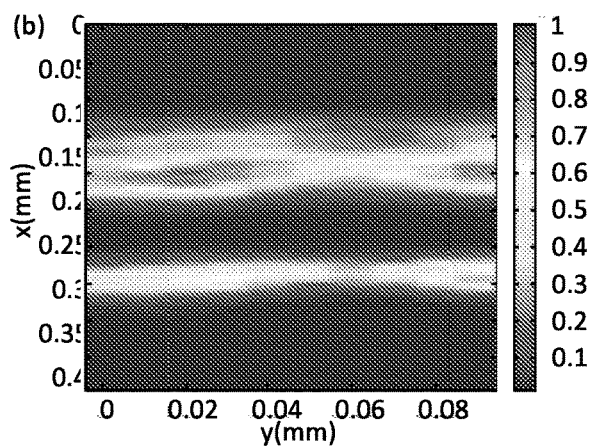
Figure 6C:
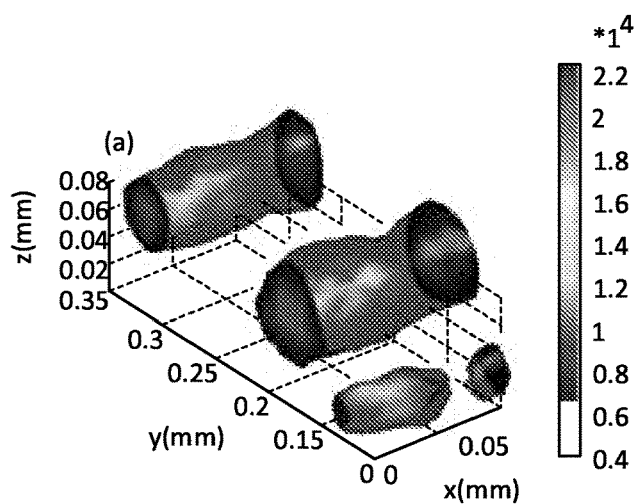
Figure 6D:
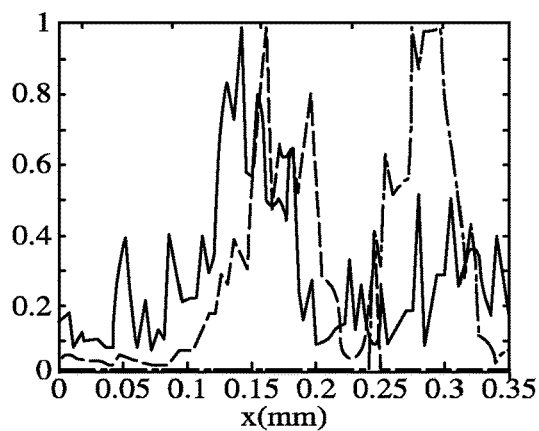
Figure 6E:
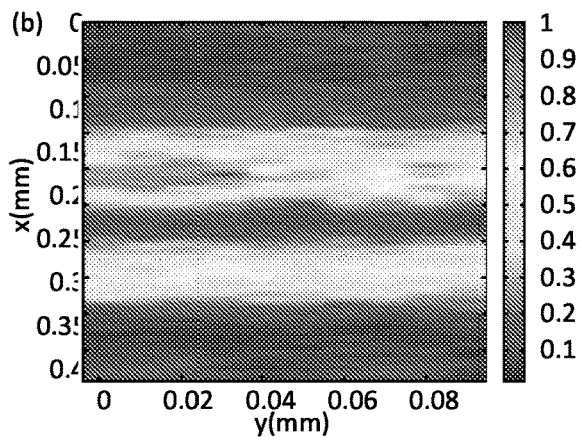
Figure 6F:
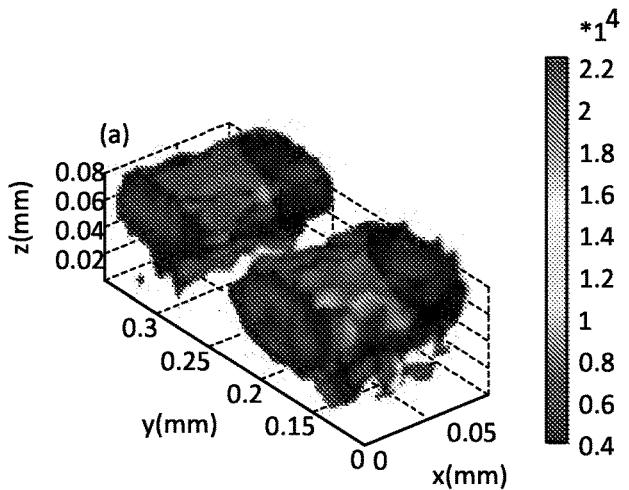
Figure 7:
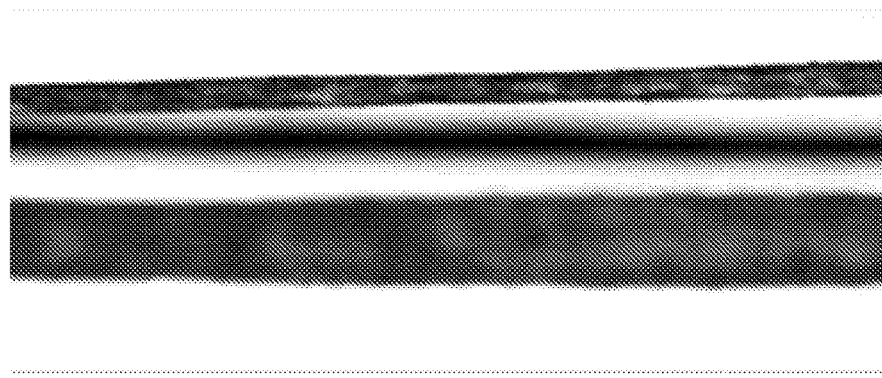
FIG. 7 shows an image from an optical microscope that shows the thickness of the hairs used in FIGS. 6A-6F according to some embodiments described herein.

FIGS. 6A-6F illustrate some of the benefits of the embodiment described herein. FIGS. 6A, 6B, and 6C show images acquired using embodiments described herein to image alpaca hairs. In some embodiments, the scatterer 125 or 225 may be a glass diffuser. The hairs being imaged have diameters of 20, 30, and 50 microns based on measurements from an optical microscope as shown in FIG. 7. FIG. 6A shows the cross section of the hairs at their depth, showing that some embodiments described herein measure a hair size which agrees with the measurements obtained via the optical microscope. In contrast, the images obtained without using the enhanced optical focus (FIGS. 6D, 6E, and 6F) broaden the dimensions of the alpaca hairs. In some embodiments, the resolutions in the images are limited by the ultrasound transducer transverse focal size (~36 microns). As shown in FIG. 6F, when the full image is reconstructed in three dimensions without wavefront optimization, two alpaca hairs are visible. As shown in FIG. 6C, all three hairs are resolved when the smaller optical focus is used and/or with wavefront optimization.

In some embodiments, optical interaction with the scatterer 125 may produce a speckle field that is detected by the transducer 135. The speckle field, for example, can be an intensity pattern produced by the mutual interference of a set of wavefronts during and/or after interaction with the scatterer 125 and/or with other portions of the photoacoustic system 100. In some embodiments, the speckle pattern may be a subjective speckle field, an objective speckle field, and/or a near-field speckle field. The speckle field caused by the scatterer 125 can cause a number of problems in imaging the sample 130.

FIG. 8 is a flowchart of the process 800 for returning an optimized image of a sample imaged through the scatterer 125 according to some embodiments described herein. One or more steps of the process 800 may be implemented, in some embodiments, by one or more components of a computational system 1600 of FIG. 16 and/or the feedback system 140. Although illustrated as discrete blocks, various blocks may be divided into additional blocks, combined into fewer blocks, or eliminated, depending on the desired implementation.

The process 800 begins at block 805. At block 805 the next SLM matrix can be retrieved from a population of SLM matrices. The population of SLM matrices can include a plurality of matrices that can be sent to the spatial light modulator to control the operation of the spatial light modulator. In some embodiments, each value in a given SLM matrix can correspond with a pixel of the spatial light modulator and the value can correspond with an amplitude and/or phase of the light modulated and/or produced by the spatial light modulator. In some embodiments, each SLM matrix of the population of SLM matrices can be created randomly, from a previous optimization process, from practice, from previous use, from memory, etc. The population of SLM matrices can include any number of SLM matrices. At block 805 the first SLM matrix can be retrieved from the population of SLM matrices.

At block 810 the SLM matrix retrieved from the population of SLM matrices can be sent to the spatial light modulator 110. The light source 105 (e.g., a laser) may then be pulsed at block 815. The spatial light modulator may modulate the light provided by the light source 105 based on the SLM matrix and directed to illuminate the sample 130 through the scatterer 125.

At block 820 acoustic data may be received from the transducer 135. The acoustic data may include a voltage and/or current measurement based on the acoustic response of the sample to the illumination provided by the spatial light modulator 110 through the scatterer 125.

At block 825 the acoustic data may be correlated and/or stored with the SLM matrix and used to illuminate the sample 130. In some embodiments the acoustic data and/or the SLM matrix may be stored in memory (e.g., working memory 1635).

At block 830 it can be determined if each SLM matrix in the population of SLM matrices has been used or if a predetermined number of cycles of blocks 805-825 has occurred. If not, then the process 800 proceeds to block 805 and the next SLM matrix may be retrieved. If each SLM matrix in the population of SLM matrices has been used or if a predetermined number of cycles of blocks 805-825 has occurred as determined at block 830, then the process 800 proceeds to block 835.

At block 835 the population of SLM matrices can be optimized. This can occur using any number of algorithms, methods, techniques, etc. For example, each SLM matrix in the population of SLM matrices can be ranked based on the corresponding acoustic data response. For example, the SLM matrices can be ranked based on the intensity and/or magnitude of the acoustic data response. The highest ranked SLM matrices (e.g., the top 10-20%) can be used to optimize to recreate the population of SLM matrices. For example, a function operating on one or more of a percentage of the highest ranked SLM matrices can be used to create an optimized population of SLM matrices. The function may include addition, subtraction, averages, means, combinations, etc. of one or more of the highest ranked SLM matrices. Regardless of the function(s) used, the optimized population of SLM matrices may include matrices based on the previously highest ranked SLM matrices.

At block 840 it can be determined whether the process 800 should repeat with the optimized population of SLM matrices and return to block 805 where the first (the next) SLM matrix of the optimized population of SLM matrices can be retrieved. In some embodiments, the process 800 may use a counter to determine whether the process 800 repeats at block 840. In some embodiments, the process 800 may use a clock to determine whether sufficient time has passed beyond a predetermined time in order to determine whether the process 800 should repeat at block 840. In some embodiments, the process 800 may compare an average acoustic data value, a mean acoustic data value, a median acoustic data value, a variance of the acoustic data value, or any other function of the acoustic data value with a predetermined threshold value to determine whether the process 800 should repeat at block 840.

In some embodiments, blocks 805-830 and/or blocks 805-840 may execute in a single repetition cycle of the light source 105. For example, if the laser is in operation at a repetition rate of 20 Hz, then blocks 805-830 and/or blocks 805-840 may repeat 20 times a second to allow each illumination of the light source 105 to correspond with a different SLM matrix.

Once it has been determined that the process 800 may not repeat at block 840, then the process 800 may proceed to block 845. At block 845 it can be determined if another sample position should be imaged. Often, only a portion of the sample may be imaged at a given time. For example, the transducer 135 may be focused on a specific portion of the sample during the first iteration or on a target area near the sample. If all the samples have not yet been imaged, then the process 800 should proceed to block 850 where either the sample 130 may be physically moved and/or the transducer 135 focus may be moved to ensure that another portion of the sample is imaged by the transducer in blocks 805-840.

The process 800 may repeat until all the sample positions have been imaged by the transducer 135. The process 800 may end at block 855 where the optimized acoustic data for each sample position is returned and/or an image created from the optimized acoustic data for each sample position may be returned.

In some embodiments, two dimensional images may be obtained by plotting the amplitude or intensity of the optimized photoacoustic response (measured at each transducer position) at a given arrival time or within a narrow time window. The depth at which a particular image is constructed is related to the arrival time through the speed of sound in the media. Three dimensional images are constructed by combining two dimensional images obtained at various (adjacent) depths. The arrival time thus yields the depth information.

Figure 9A:
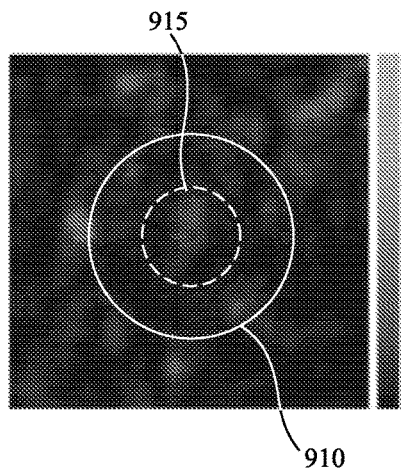
FIGS. 9A-9D illustrate the relationship between optical intensity distribution and acoustic intensity distribution according to some embodiments described herein.
Figure 9B:
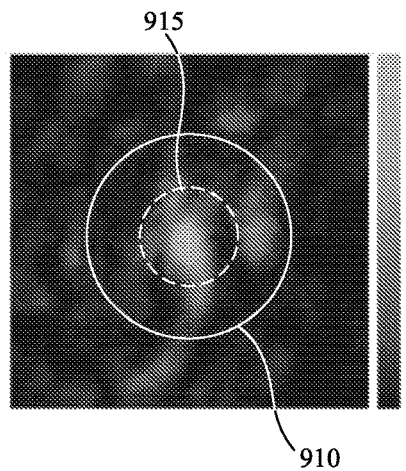
Figure 9C:
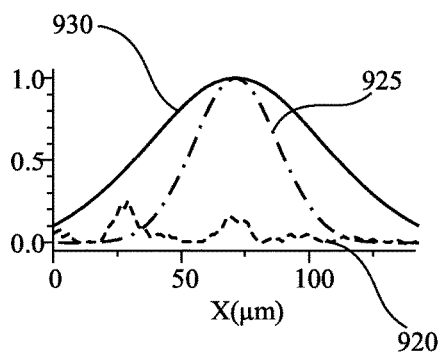
Figure 9D:
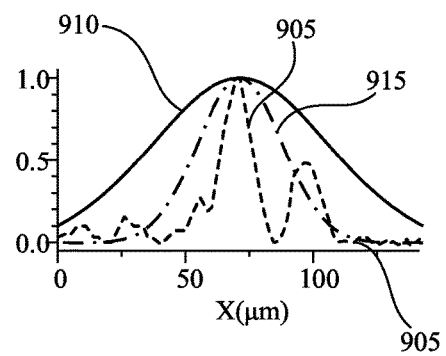

FIGS. 9A-9D illustrate the relationship between optical intensity distribution and acoustic sensitivity of the transducer according to some embodiments described herein. FIG. 9A shows an example image of a speckle field prior to optimization and FIG. 9C shows a graph of the cross section of the focus region mapping intensity versus distance. The lines 910 and 915 in FIG. 9A and/or FIG. 9B represent the spatial intensity of the transducer focus region at ultrasound frequencies of 50 MHz (central frequency of the received photoacoustic signal) and 80 MHz (frequency used for feedback optimization), respectively. Various other frequencies may be used. The lines 930 and 925 in FIG. 9C and/or FIG. 9D show the cross section of the transducer focal region at ultrasound frequencies of 50 MHz (central frequency of the received photoacoustic signal) and 80 MHz (frequency used for feedback optimization), respectively. The line 920 shows the optical intensity distribution and demonstrates that the light is not focused in the absence of wavefront optimization.

Some embodiments described herein can return a focused intensity distribution through the scatterer 125 using wavefront optimization. FIG. 9B shows an example image of a speckle field with wavefront optimization and FIG. 9D shows a graph of the cross section of the focus region mapping intensity versus distance with wavefront optimization. As shown in FIG. 9D, the intensity distribution illustrated by the line 905 shows a focused optical intensity distribution.

In some embodiments, the spatial light modulator 110 can use wavefront shaping to control the speckle field in such a way as to place a single high intensity speckle within the ultrasound transducer focus. This may, for example, improve the resolution to optical speckle size and/or improve the signal-to-noise ratio. In some embodiments, wavefronts can be optimized using, for example, a genetic algorithm with spatially non-uniform photoacoustic as an input to the genetic algorithm.

As shown in FIG. 9A, as the speckle spot size decreases relative to the acoustic focus, the photoacoustic enhancement decreases rapidly. As shown in FIG. 9B, however, the optical enhancement also decreases with decreasing speckle size, but the rate of decrease is significantly less. This can indicate, for example, that regardless of a small speckle size comparable to the acoustic feedback, an optical focus can be created. Furthermore, the size of the created focus may be a single speckle at the center of the acoustic focus. Thus, despite optimizing the wavefront with an acoustic size feedback, the light is localized to a single speckle creating an optical focus. In some embodiments, a focus may be created from multiple speckles such as, for example, using multiple smaller speckles to focus the light.

Figures 10A, 10B:
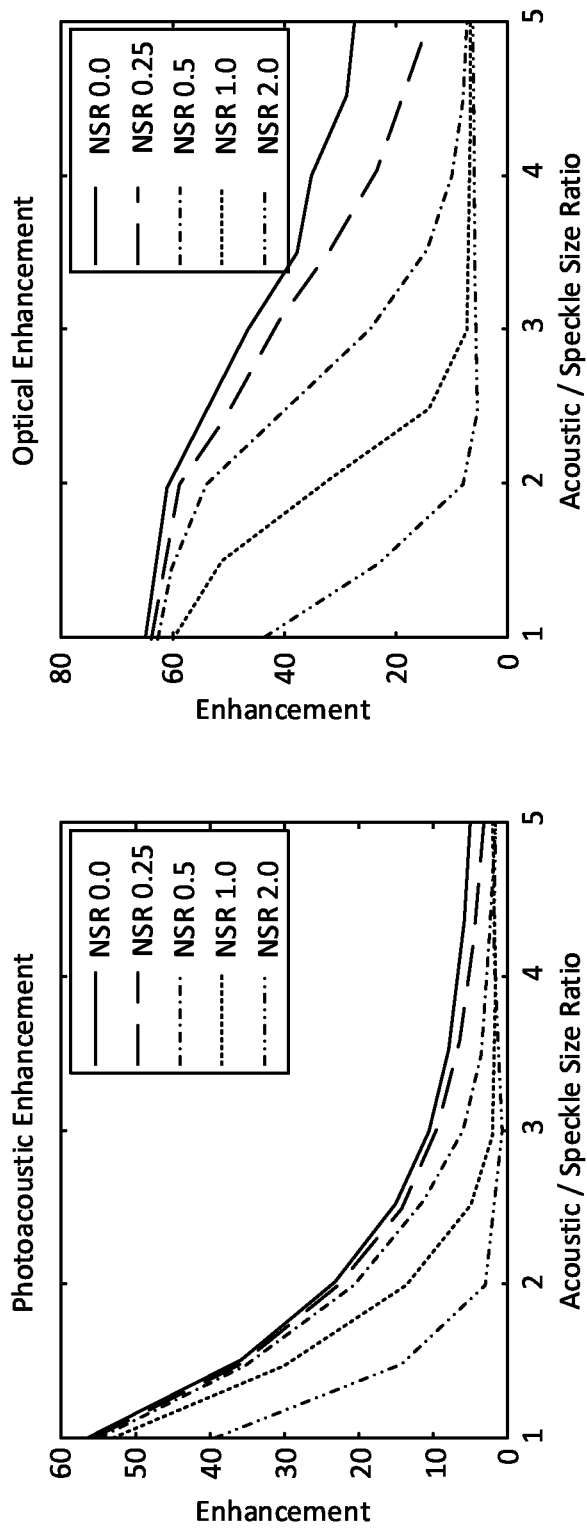
FIGS. 10A and 10B are graphs showing results of photoacoustic and optical enhancements through an optimization algorithm with various acoustic focus to speckle size ratios and noise-to-signal ratios using the embodiments described herein.

FIGS. 10A and 10B are graphs showing results of photoacoustic and optical enhancements through an optimization algorithm with various acoustic focus-to-speckle-size ratios and noise-to-signal ratios using embodiments described herein.

Figure 11B:
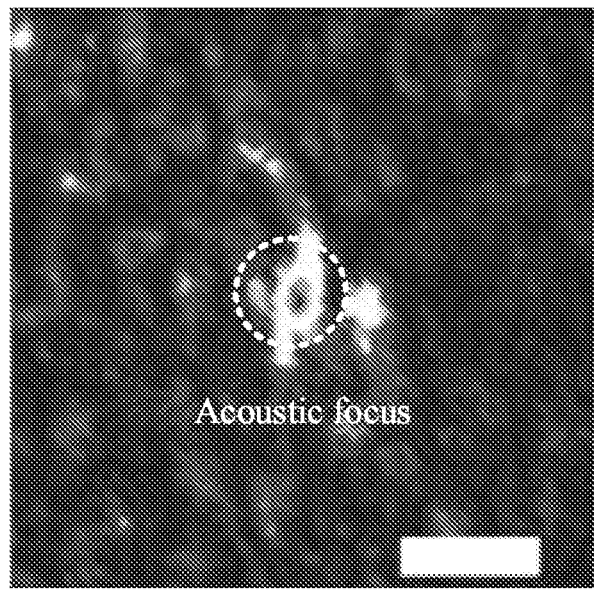
FIG. 11B shows an image of the target area including the sample using the embodiments described herein including wavefront optimization.
Figure 11A:
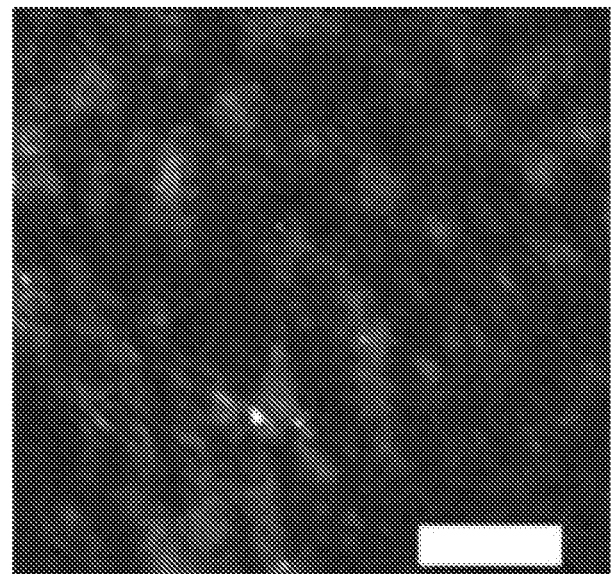
FIG. 11A shows an image of a target area including a sample without using the embodiments described herein including wavefront optimization.

FIG. 11A shows an image of a target area including a sample without using embodiments described herein including wavefront optimization. FIG. 11B shows an image of the target area including the sample using embodiments described herein including wavefront optimization. As shown in FIG. 11B, the acoustic focus is illustrated with a dashed circle in the center of the figure and an image of the sample is clearly visible within the acoustic focus.

To demonstrate the effectiveness of embodiments described herein, a 50 µm black alpaca hair was selected as a sample for photoacoustic feedback and placed behind a scatterer. In this example, the large diameter hair was selected to overfill both the acoustic transducer focal region (e.g., 36 µm) and the speckle spot size (~15 µm). This ensured that the optimization feedback included many speckles, all contributing to the photoacoustic signal. After photoacoustic optimization the photoacoustic signal was enhanced by ~8 (see, e.g., FIG. 3A). The FWHM of the focused speckle spot was 13 microns, which, in this example, is much smaller than the acoustic transducer size. The measured optical enhancement was 13, over twice the photoacoustic enhancement. Despite the larger absorber and larger acoustic feedback, a small, single speckle optical focus was created with optical enhancement higher than photoacoustic enhancement as the simulations indicated.

Figure 12A:
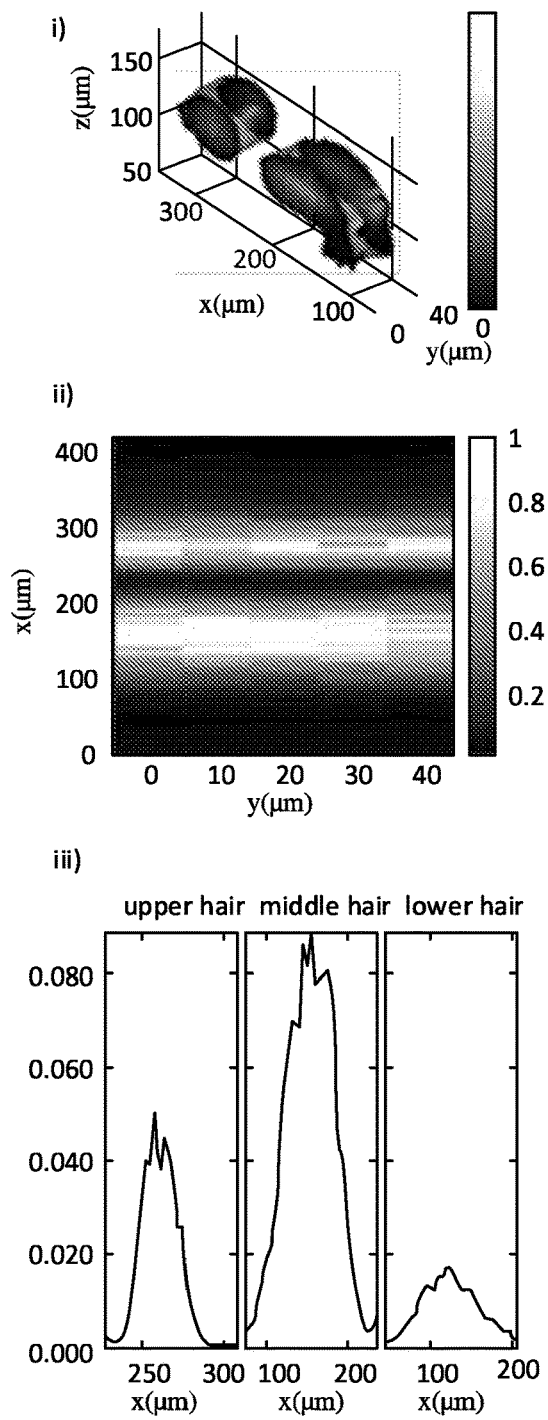
FIGS. 12A-C illustrate some results of an imaging example performed on alpaca hair using the embodiments described herein.
Figure 12B:
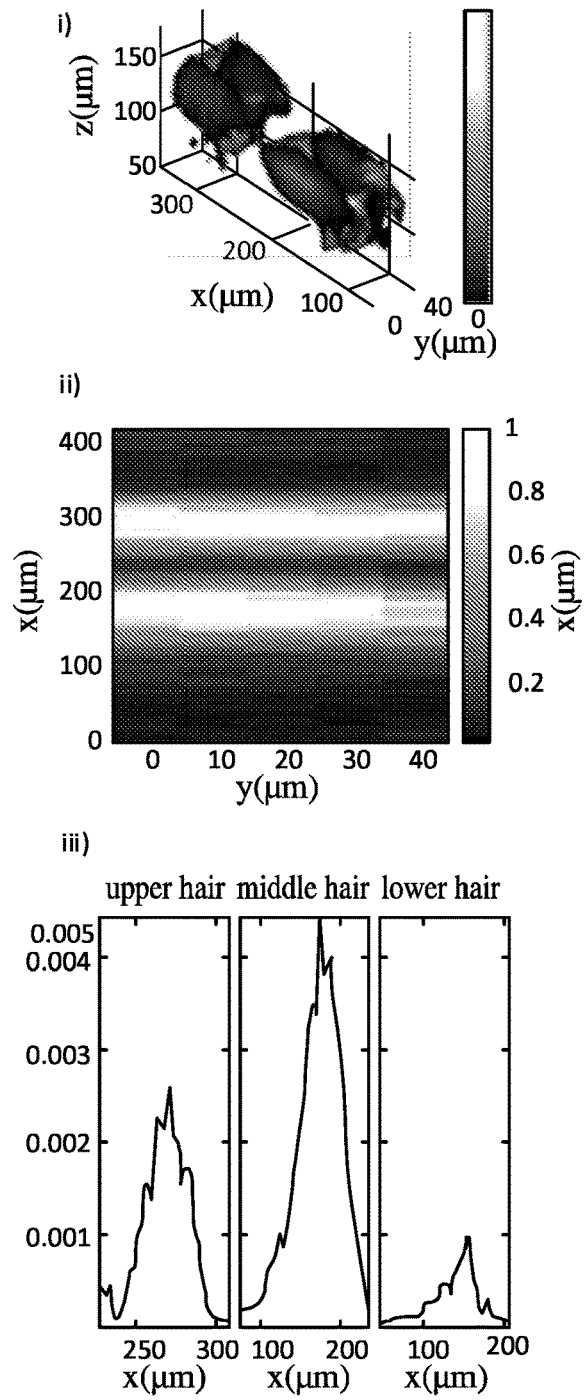
Figure 12C:
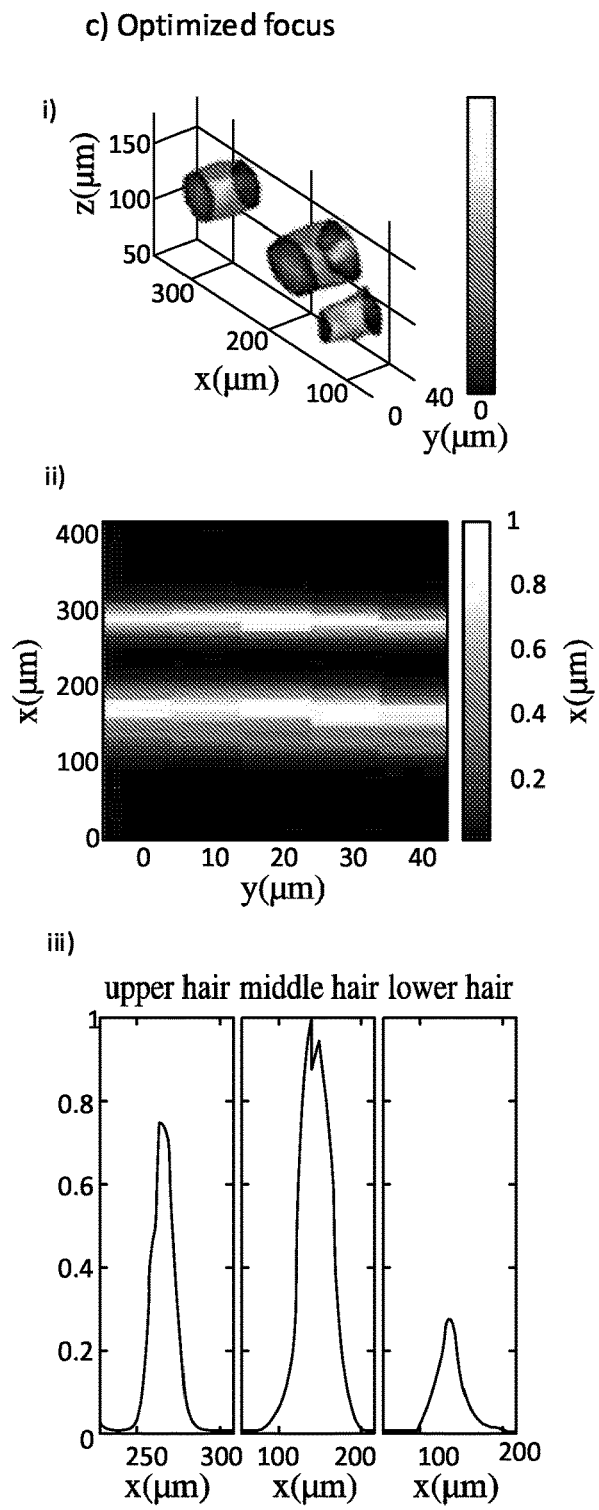

FIGS. 12A-C illustrate some results of an imaging example performed on alpaca hair using embodiments described herein. Three alpaca hairs (diameters 20, 30, and 50 µm, +/−5 µm) were placed near each other behind the scatterer 125 in the photoacoustic system 200 shown in FIG. 2. A fourth hair (diameter 50 µm) was also placed near the hairs for optimization but was not imaged. After optimization the hair sample was scanned through the optimized focus, and the photoacoustic signal was recorded for each position and processed to reconstruct an image. For comparison the hairs were also imaged with a flat phase wavefront (providing a random speckle field) and a uniform optical field. The results are shown in FIGS. 12A, 12B, and 12C. Using the optimized focal spot the measured hair diameters were 29, 30, and 45 μm, while the uniform field yielded 72, 52, and 72 μm and the speckle field 45, 70, and 57 μm. As shown in FIG. 12C, embodiments described herein can provide better imaging.

FIGS. 13A-13G show the results of an imaging example performed on a fly wing (e.g., Musca Domestica) using embodiments described herein. The fly wing was mounted and placed behind the scattering medium. The large vein on the leading edge of the wing was used for wavefront optimization focusing. The fly wing was then imaged by scanning it behind the scatterer. For comparison the wing was also imaged with a flat phase wavefront, i.e., a random speckle field. Wavefront optimization provided an SNR improvement of ~6. Additionally, the resolution of the photoacoustic image was improved with optimization, as shown in FIGS. 13A-13G. However, both images, flat phase and optimized, where able to resolve structures less than the acoustic focus. The ability to improve resolution with the flat phase is a result of the random speckle field containing one or two speckles that overpowered the rest of the speckles within the acoustic focus. This result is not highly repeatable as it is governed by the randomness of the speckle field. However, the optimization provided further resolution enhancement, 5 μm in the x-direction and 11 μm in the y-direction, as the light was focused to a single speckle.

Embodiments of the invention include techniques that rely on spatially varying feedback signals to optimize the optical wavefront such that the light was enhanced and focused to a single speckle behind a scattering medium. Embodiments of the invention create an optical focal spot ~3 times smaller than the acoustic feedback diameter. The formation of this focus can allow for imaging-absorbing samples at a higher resolution and SNR than possible without the scatterer. This method has the potential to increase the depth of optical resolution photoacoustic microscopy by providing high intensity optical foci deeper into tissue. It also provides a way to look through a scattering wall with higher resolution than the detection mechanism would otherwise allow.

FIGS. 14A-C illustrate an example image of sweat bee wing hair according to some embodiments described herein. FIG. 14C shows a photoacoustic image superimposed with an optical image. FIG. 14A shows a subset of the optical image shown in FIG. 14C and shows only the hairs of the sweat bee wing. FIG. 14B shows the corresponding photoacoustic image obtained using embodiments described herein. A normalized cross correlation analysis of the images in FIG. 14A and FIG. 14B reveals a strong correlation when they overlap, indicating the photoacoustic signatures correspond to the hairs. The scale of FIG. 14A and FIG. 14B is 20 μm. The image of the bee wing was performed by scanning the bee wing behind the scatterer. The photoacoustic image significantly improves after optimization in either or both the resolution and SNR, which can facilitate 3D image reconstruction by sectioning the photoacoustic waveform temporally.

In applications involving imaging inside or through turbid media (e.g., scatterer 110), one rarely has the ability to scan an object through a single focused point. In some embodiments, the transducer can be scanned and the wavefront can be optimized at each transducer position; thereby building an image point-by-point. In some embodiments, the wavefront can be optimized on a uniform, extended absorber and the spatial sensitivity of the transducer can lead to a preferred optical focus at the center of the acoustic focus after optimization.

Figure 15A:
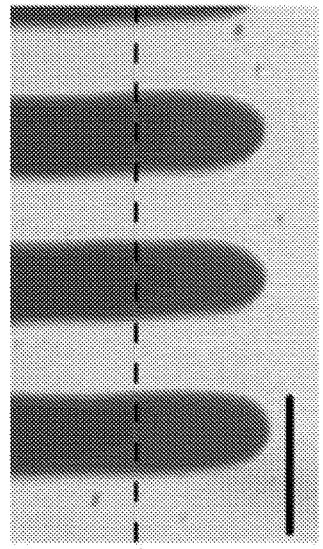
FIGS. 15A-D illustrates an absorber jumping method according to some embodiments described herein.

If the wavefront is not optimized on an extended absorber, then the optimization routine may produce an optical focus at the position within the transducer focal region that produces the largest measured photoacoustic response. This response may depend on both the absorbed optical energy distribution and/or a transducer point spread function. As the transducer is scanned to build up a photoacoustic image the exact location of the focus may not be known at each step. Nevertheless, in some embodiments, an optical focus may be produced that jumps from absorber to absorber to maximize the photoacoustic response while delivering significant spatial information as shown in FIG. 15A.

Figure 15B:
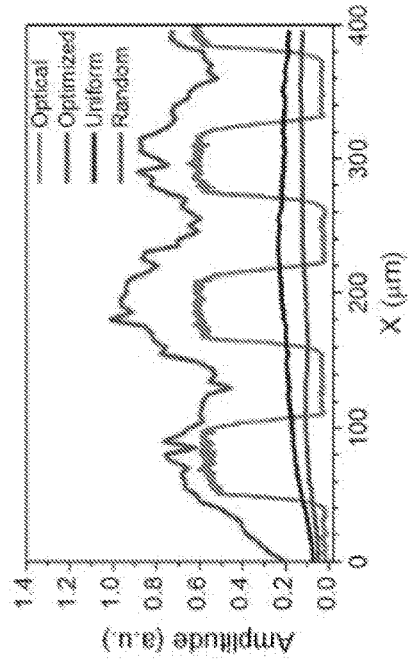
Figure 15C:
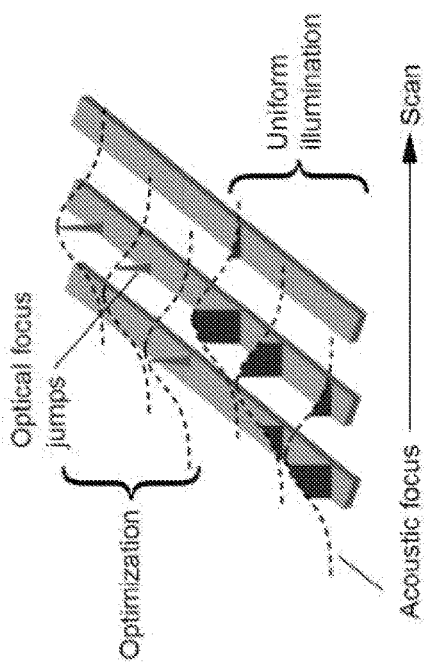
Figure 15D:
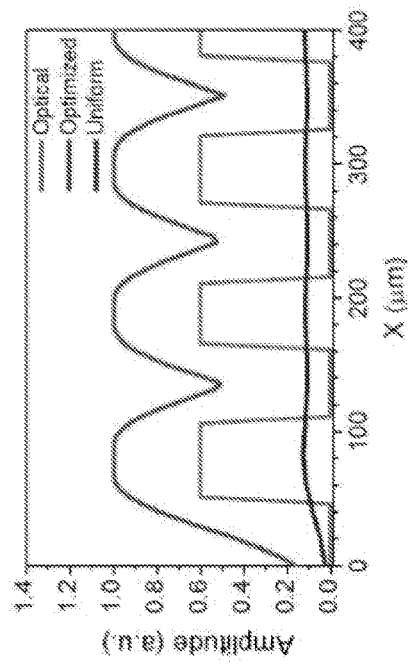

FIG. 15B shows an image of target that is scanned by jumping from absorber to absorber as described above. As shown in FIG. 15B, in this example, the target includes of 55±3 μm wide chromium bars separated by 55±3 μm. FIG. 15C illustrates the photoacoustic response to uniform and optimized illumination fields as the transducer is scanned across the target. This indicates that the optimized focus improves the ability to resolve the individual bars, which may be a direct result of having a tight focus that seeks the strongest absorber rather than a response integrated over the entire focal volume. FIG. 15D shows the results of using this method, which shows good agreement with theory. As shown the optimized wavefront produces an enhanced photoacoustic response and/or may allow for the individual bars to be resolved.

Moreover, in some embodiments, the frequency spectra of the photoacoustic signals generated by the optimized wavefront showed an enhanced high frequency response with respect to those with uniform illumination.

Figure 16:
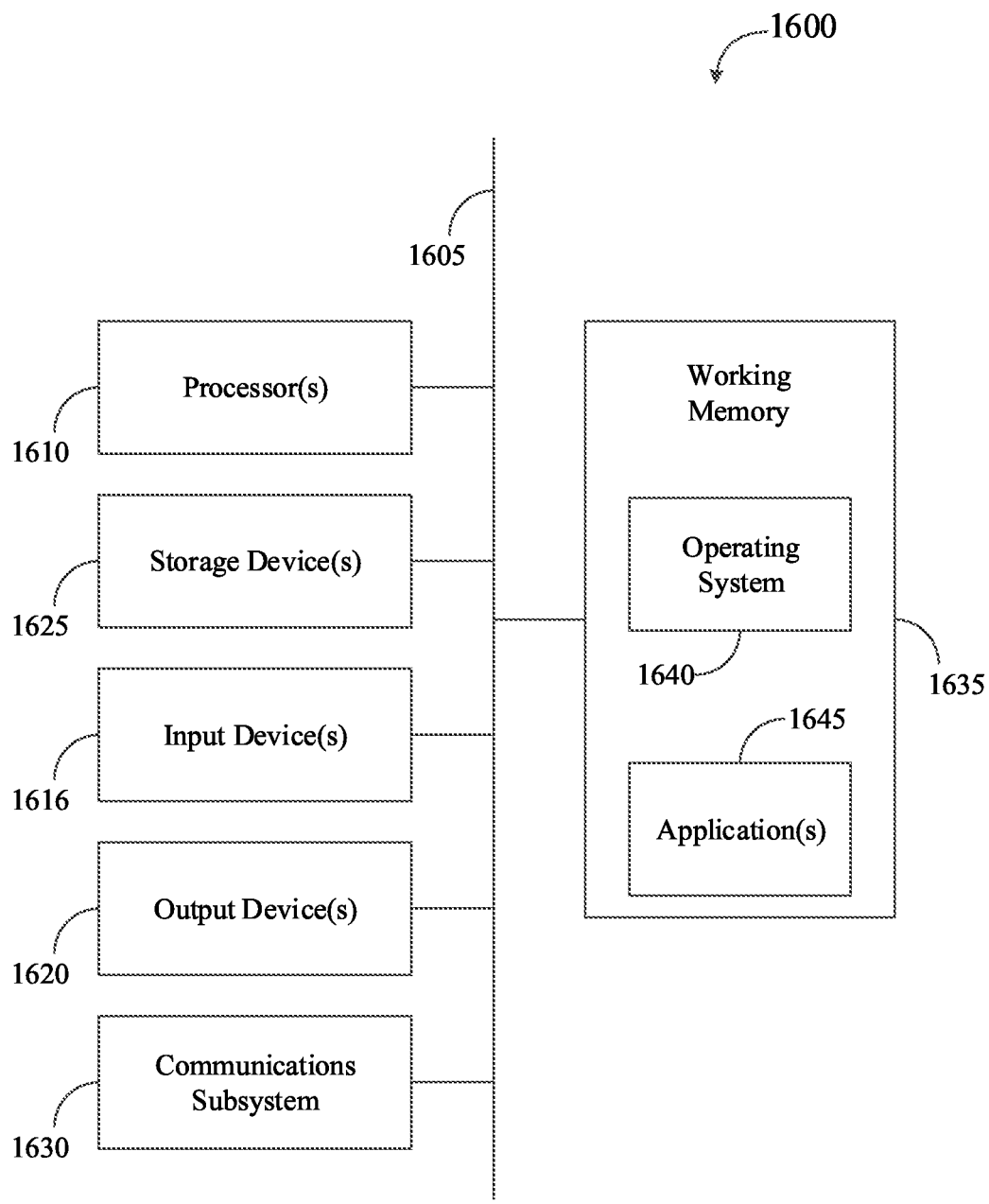
FIG. 16 is a block diagram of a computer system that can be used in conjunction with some embodiments described herein.

The computational system 1600 (or controller or processor) shown in FIG. 16 can be used to perform any of the embodiments of the invention. For example, the computational system 1600 can be used to execute the various methods, processes, inferences, decisions, and/or calculations described herein. As another example, the computational system 1600 can be used to perform any calculation, identification, and/or determination described herein. The computational system 1600 includes hardware elements that can be electrically coupled via a bus 1605 (or may otherwise be in communication, as appropriate). The hardware elements can include one or more processors 1610 including, without limitation, one or more general-purpose processors and/or one or more special-purpose processors (such as digital signal processing chips, graphics acceleration chips, and/or the like); one or more input devices 1615, which can include, without limitation, a mouse, a keyboard, and/or the like; and one or more output devices 1620, which can include, without limitation, a display device, a printer, and/or the like.

The computational system 1600 may further include (and/or be in communication with) one or more storage devices 1625, which can include, without limitation, local and/or network-accessible storage and/or can include, without limitation, a disk drive, a drive array, an optical storage device, a solid-state storage device, such as a random access memory ("RAM") and/or a read-only memory ("ROM"), which can be programmable, flash-updateable, and/or the like. The computational system 1600 might also include a communications subsystem 1630, which can include, without limitation, a modem, a network card (wireless or wired), an infrared communication device, a wireless communication device and/or chipset (such as a Bluetooth device, an 802.6 device, a Wi-Fi device, a WiMax device, cellular communication facilities, etc.), and/or the like. The communications subsystem 1630 may permit data to be exchanged with a network (such as the network described below, to name one example) and/or any other devices described herein. In many embodiments, the computational system 1600 will further include a working memory 1635, which can include a RAM or ROM device, as described above.

The computational system 1600 also can include software elements, shown as being currently located within the working memory 1635, including an operating system 1640 and/or other code, such as one or more application programs 1645, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1625 described above.

In some cases, the storage medium might be incorporated within the computational system 1600 or in communication with the computational system 1600. In other embodiments, the storage medium might be separate from the computational system 1600 (e.g., a removable medium, such as a compact disc, etc.) and/or provided in an installation package, such that the storage medium can be used to program a general-purpose computer with the instructions/code stored thereon. These instructions might take the form of executable code, which is executable by the computational system 1600 and/or might take the form of source and/or installable code, which, upon compilation and/or installation on the computational system 1600 (e.g., using any of a variety of generally available compilers, installation programs, compression/decompression utilities, etc.) then takes the form of executable code.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

That which is claimed:

1. A method for sub-acoustic focusing, the method comprising:
   illuminating a sample through a scatterer using a light source and at least one spatial light modulator;
   receiving a photoacoustic signal from a transducer;
   determining an optimized wavefront from the photoacoustic signal;
   modifying a configuration of the spatial light modulator based on the optimized wavefront; and
   illuminating the sample through the scatterer using the light source and the spatial light modulator with the modified configuration, wherein the modified configuration produces an optical focus that is smaller than an acoustic focus of the transducer.

2. The method according to claim 1, wherein the spatial light modulator is an optical element selected from the group consisting of one or more spatial light modulators, phase-only spatial light modulators, intensity-only spatial light modulators, prism arrays, diffractive elements, diffusers, holograms, Dammann gratings, liquid crystal spatial light modulators, phase masks, amplitude masks, acousto-optic modulator, acousto-optic deflector, and phase/amplitude masks.

3. The method according to claim 1, wherein the determining the optimized wavefront includes using an optimization algorithm to determine the optimized wavefront.

4. The method according to claim 1, further comprising scanning the sample, moving the sample with fluid, scanning a focus of the transducer, and/or scanning a focus of the light source.

5. A sub-acoustic resolution imaging system comprising:
a pulsed light source;
an optical system configured to direct light from the light source toward a sample through a scatterer;
one or more acoustic transducers configured to record acoustic signals from the sample; and
a controller coupled with at least a portion of the optical system and the one or more acoustic transducers, wherein the controller is configured to modify a phase and/or amplitude of the light directed by the optical system through the scatterer using data from the one or more acoustic transducers.

6. The imaging system according to claim 5, wherein the one or more acoustic transducers is disposed outside the scatterer such that the acoustic signals pass through the scatterer.

7. The imaging system according to claim 5, wherein the optical system comprises a spatial light modulator, one or more lenses and/or an objective lens.

8. The imaging system according to claim 5, wherein the optical system includes an optical element selected from the group consisting of one or more spatial light modulators, phase-only spatial light modulators, intensity-only spatial light modulators, prism arrays, diffractive elements, diffusers, holograms, Dammann gratings, liquid crystal spatial light modulators, phase masks, amplitude masks, acousto-optic modulator, acousto-optic deflector, and phase/amplitude masks.

9. The imaging system according to claim 5, wherein the controller is configured to use an optimization algorithm based on the data from the one or more acoustic transducers to modify the phase and/or amplitude of the light.

10. The imaging system according to claim 5, wherein the controller is configured to use spatially varying feedback to optimize an optical wavefront from the optical system such that the light is enhanced and focused to a single speckle behind the scatterer.

11. The imaging system according to claim 5, wherein the controller is configured to increase a depth of optical resolution photoacoustic microscopy by providing high intensity optical focus.

12. The imaging system according to claim 5, wherein the controller is configured to scan the sample, scan a focus of the one or more transducers, and/or scan a focus of the light source.

13. A method for focusing with sub-acoustic resolution, the method comprising:
illuminating a sample inside a scatterer with a plurality of optical wavefronts modulated by a spatial light modulator, each of the plurality of optical wavefronts produced modulated by the spatial light modulator using one of a plurality of SLM matrices selected from a population of SLM matrices;
receiving a plurality of electric signals from a transducer, wherein each of the plurality of electric signals correspond with a photoacoustic signal received at the transducer for each of the plurality of optical wavefronts such that the transducer receives a plurality of photoacoustic signals; and
determining an optimum SLM matrix from the population of SLM matrices based on the plurality of electric signals, wherein the optimum SLM matrix produces an optical focus at or near the sample that is smaller than an acoustic focus of the transducer.

14. The method according to claim 13, wherein the determining an optimum SLM matrix from the population of SLM matrices comprises determining an optimum SLM matrix from the population of SLM matrices using a genetic algorithm.

15. The method according to claim 13, wherein the determining an optimum SLM matrix from the population of SLM matrices based on the plurality of electric signals comprises determining an optimum SLM matrix from the population of SLM matrices based on a peak-to-peak voltage of the plurality of electric signals.

16. The method according to claim 13, further comprising returning an image of the sample corresponding with illumination of the sample with the optimum SLM matrix.

17. The method according to claim 13, further comprising:
scanning the sample in a x-y plane; and
repeating the method.

18. The method according to claim 13, further comprising:
moving the acoustic focus of the one or more transducers; and
repeating the method.

19. The method according to claim 13, wherein the image is a three-dimensional image of the sample.

20. The method according to claim 13, wherein the plurality of photoacoustic signals are enhanced by nonlinear effects in the sample.

* * * * *